US 6,740,028 B2

(12) United States Patent
Boone et al.

(10) Patent No.: US 6,740,028 B2
(45) Date of Patent: *May 25, 2004

(54) METHOD AND APPARATUS FOR TEMPORARILY IMMOBILIZING A LOCAL AREA OF TISSUE

(75) Inventors: Eric Boone, Comstock Park, MI (US); Jack Goodman, Ann Arbor, MI (US); John D. Hall, Mayfield Hts, OH (US); Vincent J. Testa, Mars, PA (US); Eric Vroegop, Holland, MI (US); William G. O'Neill, Maple Grove, MN (US); Cornelius Borst, Bilthoven (NL); Hendricus J. Mansvelt-Beck, Bilthoven (NL); Paul F. Gründeman, Amsterdam (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/099,177

(22) Filed: Mar. 13, 2002

(65) Prior Publication Data

US 2002/0161277 A1 Oct. 31, 2002

Related U.S. Application Data

(63) Continuation of application No. 09/396,047, filed on Sep. 15, 1999, now Pat. No. 6,464,629
(60) Provisional application No. 60/100,442, filed on Sep. 15, 1998.

(51) Int. Cl.[7] .............................. A61F 2/00; A61F 13/00

(52) U.S. Cl. ........................................................ 600/37

(58) Field of Search ........................... 600/37, 202, 201, 600/206, 229, 235; 128/898

(56) References Cited

U.S. PATENT DOCUMENTS

| 452,131 | A | 5/1891 | Haughawout |
| 3,577,982 | A | 5/1971 | La Par ........................ 128/2 R |
| 3,720,433 | A | 3/1973 | Rosfelder ................. 294/64 R |
| 3,783,873 | A | 1/1974 | Jacobs ..................... 128/303 R |
| 3,786,815 | A | 1/1974 | Ericson ........................ 128/321 |
| 3,858,926 | A | 1/1975 | Ottenhues .................. 294/64 R |
| 3,916,909 | A | 11/1975 | Kletschka et al. .......... 128/354 |

(List continued on next page.)

FOREIGN PATENT DOCUMENTS

| DE | 9004513.0 | 4/1990 |
| DE | 29708050 | 5/1997 |
| EP | 0 167 345 A1 | 1/1986 |

(List continued on next page.)

OTHER PUBLICATIONS

Mammary Artery–Coronary Artery Anastomosis as Method of Treatment for Angina Pectoris, V.I Kolessov, MD/Thoracic and Cardiovascular Surgery, vol. 54, No. 4, Oct. 1967 pp 535–544.

(List continued on next page.)

Primary Examiner—Max F. Hindenburg
Assistant Examiner—Brian Szmal
(74) Attorney, Agent, or Firm—Thomas G. Berry; Daniel W. Latham

(57) ABSTRACT

The invention is a method and apparatus for performing beating heart surgery, in which a single articulating arm supports multiple suction pods. Once the suction pods are applied to the heart surface, tightening a cable fixes the arm in place. Then, the suction pods may be spread apart from each other to tighten the surface of the cardiac tissue lying between the suction pods. In one embodiment, fixation of the arm as well as the spreading apart of the suction pods may occur concurrently or almost concurrently through the tensioning of a single cable. Additional embodiments of the method, system and its components are shown.

22 Claims, 24 Drawing Sheets

U.S. PATENT DOCUMENTS

| | | | |
|---|---|---|---|
| 3,951,138 A | 4/1976 | Akopov | 128/17 |
| 3,983,863 A | 10/1976 | Janke et al. | 128/1 R |
| 3,999,795 A | 12/1976 | Barker | 294/64 R |
| 4,047,532 A | 9/1977 | Phillips et al. | 128/303 R |
| 4,049,002 A | 9/1977 | Kletschka et al. | 128/318 |
| 4,096,864 A | 6/1978 | Kletschka et al. | 128/354 |
| 4,306,561 A | 12/1981 | de Medinaceli | 128/303.13 |
| 4,314,568 A | 2/1982 | Loving | 128/327 |
| 4,350,160 A | 9/1982 | Kolesov | 128/334 R |
| 4,366,819 A | 1/1983 | Kaster | 128/334 C |
| 4,368,736 A | 1/1983 | Kaster | 128/334 C |
| 4,447,227 A | 5/1984 | Kotsanis | 604/95 |
| 4,463,980 A | 8/1984 | Orii | 294/64 R |
| 4,627,421 A | 12/1986 | Symbas et al. | 128/20 |
| 4,637,377 A | 1/1987 | Loop | 128/1 R |
| 4,646,747 A | 3/1987 | Lundbáck | 128/643 |
| 4,688,570 A | 8/1987 | Kramer et al. | 128/305 |
| 4,711,247 A | 12/1987 | Fishman | 128/743 |
| 4,718,418 A | 1/1988 | L'Esperance, Jr. | 128/303.1 |
| 4,726,356 A | 2/1988 | Santilli et al. | 128/20 |
| 4,736,749 A | 4/1988 | Lundback | 128/643 |
| 4,767,142 A | 8/1988 | Takahashi et al. | 294/64.1 |
| 4,808,163 A | 2/1989 | Laub | 604/105 |
| 4,854,318 A | 8/1989 | Solem et al. | 128/346 |
| 4,865,019 A | 9/1989 | Phillips | 128/20 |
| 4,892,343 A | 1/1990 | Hall | 294/64.1 |
| 4,904,012 A | 2/1990 | Nishiguchi et al. | 294/64 |
| 4,925,443 A | 5/1990 | Heilman et al. | 600/16 |
| 4,955,896 A | 9/1990 | Freeman | 606/210 |
| 4,962,758 A | 10/1990 | Lasner et al. | 128/41 |
| 4,973,300 A | 11/1990 | Wright | 600/37 |
| 4,989,587 A | 2/1991 | Farley | 128/20 |
| 4,991,578 A | 2/1991 | Cohen | 128/419 D |
| 5,009,660 A | 4/1991 | Clapham | 606/166 |
| 5,011,469 A | 4/1991 | Buckberg et al. | 604/4 |
| 5,053,041 A | 10/1991 | Ansari et al. | 606/148 |
| 5,098,369 A | 3/1992 | Heilman et al. | 600/16 |
| 5,108,412 A | 4/1992 | Krumeich et al. | 606/166 |
| 5,119,804 A | 6/1992 | Anstadt | 12/64 |
| 5,131,905 A | 7/1992 | Grooters | 600/16 |
| 5,133,737 A | 7/1992 | Grismer | 606/205 |
| 5,167,223 A | 12/1992 | Koros et al. | 128/20 |
| 5,171,254 A | 12/1992 | Sher | 606/166 |
| 5,207,467 A | 5/1993 | Smith | 294/64.1 |
| 5,287,861 A | 2/1994 | Wilk | 128/898 |
| 5,290,082 A | 3/1994 | Palmer et al. | 294/64.1 |
| 5,300,087 A | 4/1994 | Knoepfler | 606/207 |
| 5,324,087 A | 6/1994 | Shimose et al. | 294/64.1 |
| 5,336,252 A | 8/1994 | Cohen | 607/119 |
| 5,365,921 A | 11/1994 | Bookwalter et al. | 128/20 |
| 5,372,124 A | 12/1994 | Takayama et al. | 128/4 |
| 5,374,277 A | 12/1994 | Hassler | 606/207 |
| 5,383,840 A | 1/1995 | Heilman et al. | 600/17 |
| 5,417,709 A | 5/1995 | Slater | 606/205 |
| 5,425,705 A | 6/1995 | Evard et al. | 604/28 |
| 5,437,651 A | 8/1995 | Todd et al. | 604/313 |
| 5,452,733 A | 9/1995 | Sterman et al. | 128/898 |
| 5,472,438 A | 12/1995 | Schmit et al. | 606/1 |
| 5,509,890 A | 4/1996 | Kazama | 600/37 |
| 5,545,123 A | 8/1996 | Oritz et al. | 600/235 |
| 5,556,147 A | 9/1996 | Somekh et al. | 294/64.1 |
| 5,607,421 A | 3/1997 | Jeevanandam et al. | 606/15 |
| 5,613,937 A | 3/1997 | Garrison et al. | 600/201 |
| 5,667,624 A | 9/1997 | Akimoto et al. | 156/389 |
| 5,702,420 A | 12/1997 | Sterling et al. | 606/205 |
| 5,727,569 A | 3/1998 | Benetti et al. | 128/898 |
| 5,749,892 A | 5/1998 | Vierra et al. | 600/204 |
| 5,782,746 A | 7/1998 | Wright | 600/37 |
| 5,799,661 A | 9/1998 | Boyd et al. | 128/898 |
| 5,807,243 A | 9/1998 | Vierra et al. | 600/204 |
| 5,827,216 A | 10/1998 | Igo et al. | 604/21 |
| 5,836,311 A | 11/1998 | Borst et al. | 128/897 |
| 5,865,730 A | 2/1999 | Fox et al. | 600/228 |
| 5,875,782 A | 3/1999 | Ferrari et al. | 128/898 |
| 5,876,332 A | 3/1999 | Looney | 600/227 |
| 5,885,271 A | 3/1999 | Hamilton et al. | 303/1 |
| 5,891,017 A | 4/1999 | Swindle et al. | 600/205 |
| 5,894,843 A | 4/1999 | Benetti et al. | 128/898 |
| 5,906,607 A | 5/1999 | Taylor et al. | 606/1 |
| 5,927,284 A | 7/1999 | Borst et al. | 128/898 |
| 5,957,835 A | 9/1999 | Anderson et al. | 600/201 |
| 5,967,972 A | 10/1999 | Santilli et al. | 600/232 |
| 5,976,080 A | 11/1999 | Farascioni | 600/213 |
| 5,984,864 A | 11/1999 | Fox et al. | 600/201 |
| 6,007,486 A | 12/1999 | Hunt et al. | 600/205 |
| 6,015,378 A | 1/2000 | Borst et al. | 600/37 |
| 6,019,722 A | 2/2000 | Spence et al. | 600/210 |
| 6,030,340 A | 2/2000 | Maffei et al. | 600/233 |
| 6,032,672 A | 3/2000 | Taylor | 128/898 |
| 6,033,362 A | 3/2000 | Cohn | 600/213 |
| 6,036,641 A | 3/2000 | Taylor et al. | 600/231 |
| 6,063,021 A | 5/2000 | Hossain et al. | 600/37 |
| 6,071,235 A | 6/2000 | Furnish et al. | 600/235 |
| 6,102,854 A | 8/2000 | Cartier et al. | 600/228 |
| 6,110,187 A | 8/2000 | Donlon | 606/151 |
| 6,113,534 A | 9/2000 | Koros et al. | 600/213 |
| 6,139,492 A | 10/2000 | Vierra et al. | 600/204 |
| 6,338,712 B2 * | 1/2002 | Spence et al. | 600/201 |
| 6,464,629 B1 * | 10/2002 | Boone et al. | 600/37 |

FOREIGN PATENT DOCUMENTS

| | | |
|---|---|---|
| EP | 0 432 560 A2 | 11/1990 |
| EP | 0 630 629 A1 | 12/1994 |
| EP | 0 668 058 A1 | 8/1995 |
| EP | 0 791 330 | 2/1997 |
| EP | 0 808 606 A1 | 11/1997 |
| EP | 0 293 760 A3 | 5/1998 |
| EP | 0 908 139 A1 | 4/1999 |
| EP | 0 919 193 A1 | 6/1999 |
| EP | 0 920 835 A1 | 6/1999 |
| GB | 2 140 695 A | 12/1984 |
| GB | 2 214 428 A | 9/1989 |
| GB | 2 214 428 B | 6/1991 |
| GB | 2267827 | 12/1993 |
| WO | WO 87/04081 | 7/1987 |
| WO | WO 88/00481 | 1/1988 |
| WO | Wo 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/40751 | 11/1997 |
| WO | WO 98/10705 | 3/1998 |
| WO | WO 98/17182 | 4/1998 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |

OTHER PUBLICATIONS

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974–978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108–109.

A Prospective Evaluation of the Pulsatile Assist Device, GL Zumbro, Jr., MD; G Shearer, CCP; ME Fishback, MD; and RF Galloway, MD / The Annals of Thoracic Surgery, Vol 28, No. 2 Aug. 1979, pp. 269–273.

Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304–309.

Coronary Artery Revascularization Without Cardiopulmonary Bypass, R. Archer DO; Da Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52–57.

Direct Myocardial Revascularization Without Cardiopulmonary Bypass, E. Buffalo; JCS Andrade, J Succi; LEV Leao; and C Gallucci. Thoac. Cardiovasc. Surgeon, 33 (1985) pp. 26–29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May–Jun. 1985, pp. 217–222.

Heart–Mechanical Assist Device Interaction, JY Kresh; PLM Kerkhof; SM Goldman; and SK Brockman, Trans. Am. Soc. Artif. Intern. Organs, Vol XXXII, 1986, pp. 437–443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710–712

Long–Term Follow–up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116–124.

Extended Clinical Support with an Implantable Left Ventricular Assist Device, MG McGee; SM Parnis; T Nakatani; T Myers; K Dasse; WD Hare; JM Duncan; VL Poirier; and OH Frazier, Trans Am. Soc. Artif. Intern. Organs, Vol XXXV, 1989, pp. 614–616.

Current Status of Cardiac Surgery: A 40–Year Review, WE Richenbacher, MD; JL Myers, MD, FACC; JA Walhausen, MD, FACC, Journal of American College of Cardiology, vol. 14, No. 3, Sep. 1989, pp. 535–544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, Vol 38 (1990) pp. 69–72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti MD; G Naselli, MD; M Wood, MD; and L Geffner, MD, Chest, vol. 100. No. 2, Aug. 1991, pp. 312–316.

Coronary Artery Bypass Without Cardiopulmonary Bypass, Pfister et al, The Annals of Thoracic Surgery, vol. 54 #6 Dec. 1992 pp. 1085–1092.

Coronary Artery Operation Supported by the Hemopump: An Experimental Study on Pig, U Lonn, MD; B Peterzen, MD; H Granfeldt, MD; and H Casimir–Ahn, MD, Ph.D. The Annals of Thoracic Surgery, vol. 58, No. 1, Jul. 1994, pp. 516–523.

Regional Cardiac Wall Immobilization for Open Chest and Closed Chest Coronary Artery Bypass Grafting on the Beating Heart: The 'Octopus' Method, Circulation, vol 92. No. 8 Supplement 1, I–177 (Oct. 15, 1995).

A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I–176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356–1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486–489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570–575.

Transcatheter Radiofrequency Ablation of Atrial Tissue Using a Suction Catheter, Th Lavergne et al (PACE, vol. 12, Jan. 1989, Part II, pp. 177–186.

Abstract: "Closed Chest Coronary Artery Bypass With Cardioplegic Arrest in the Dog", Stevens et al. $67^{th}$ Scientific Sessions.

Placement of Coronary Artery Bypass Graft without Pump Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Gründeman; DW Meijer; JJG Bannenberg; R tukkie; and PJ Klopper, Surgical Endoscopy (1993) 7: 511–513.

The Last Operation: Techniques and Results Before and After the Stabilization Era, Antonio M. Calafiore, MD; Giuseppe Vitolla, MD; Valerio Massei, MD; Giovanni Teodori, MD; Gabriele Di Giammarco, MD; Teresa Iovino, MD and Angela Iaco, MD; Ann Thorac Surg 1998; 66:998–1001.

Hybrid–Type Stabilizer for Off–Pump Direct Coronary Artery Bypass Grafting, By: Toshio Konishi, M.D.; Kazuhiko Higuchi, M.D.; Mutumu Fukata, M.D.; Shinji Akisima, M.D.; and Shoji Fukuda, M.D.; Ann Thorac Surger 1998; 66:961–2.

* cited by examiner

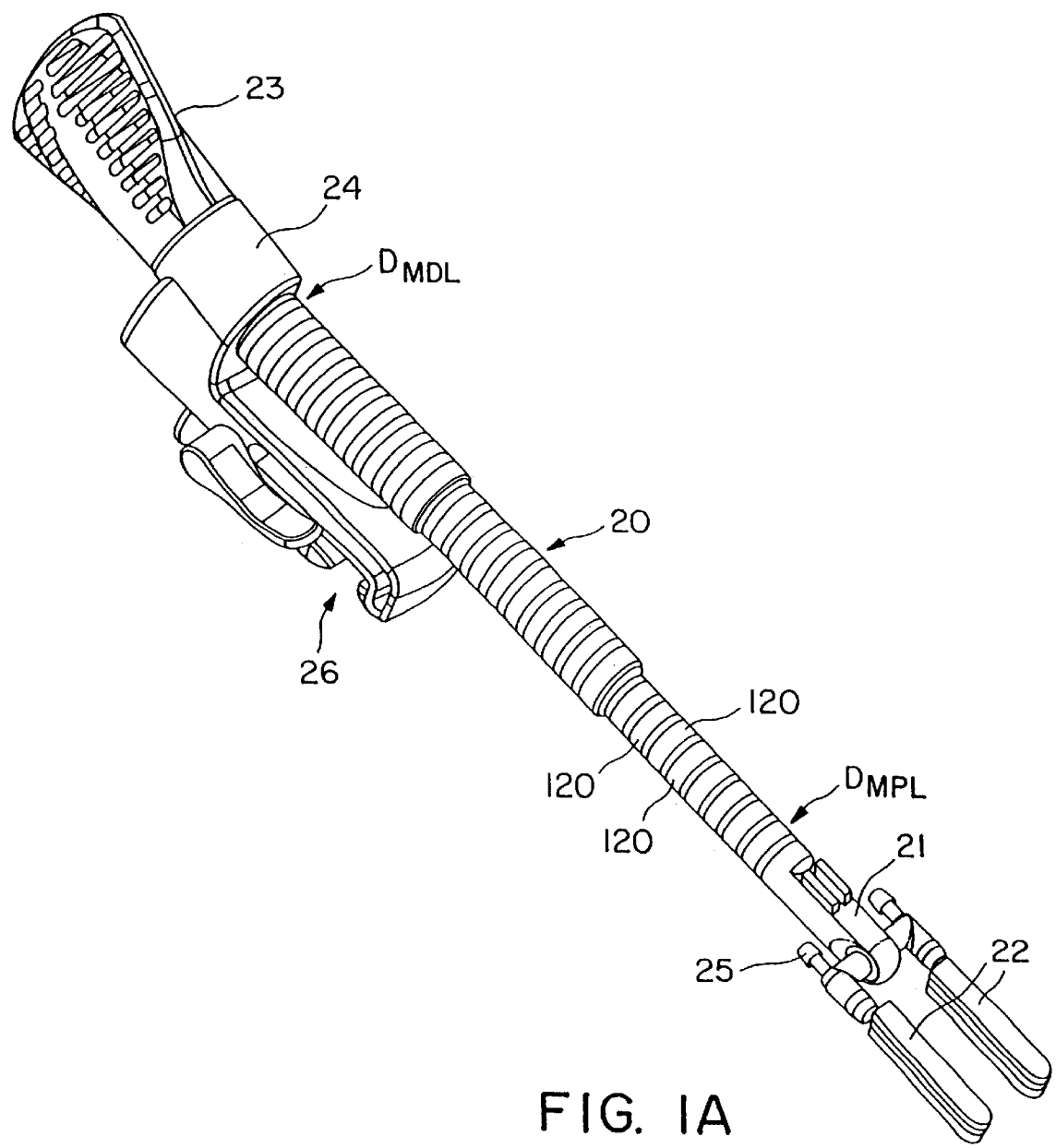
FIG. IA

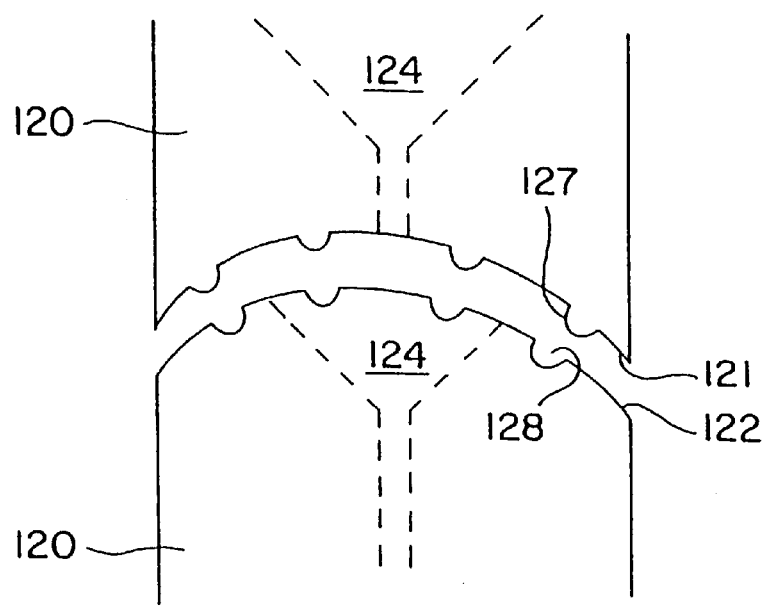
FIG. IE
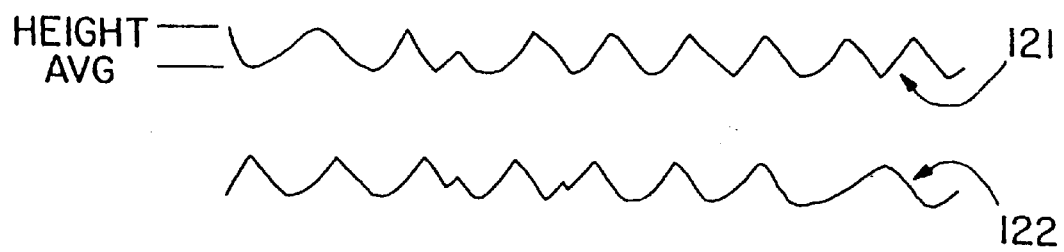
FIG. ID

METHOD AND APPARATUS FOR TEMPORARILY IMMOBILIZING A LOCAL AREA OF TISSUE

This application is a continuation of application Ser No. 09/396,047, filed Sep. 15, 1999 now U.S. Pat. No. 6,464,629, which claims benefit of No. 60/100,442 filed Sep. 15, 1998.

FIELD OF THE INVENTION

The present invention generally relates to surgery on body tissues and organs. More specifically, the present invention relates to a method and apparatus for temporarily immobilizing a local area of tissue subject to motion, such as the heart wall, which permits a surgical procedure to be performed on that local area of tissue.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally consists of the following steps: First, direct access to the heart is achieved. This is usually done by opening the chest by median sternotomy and spreading the left and right rib cage apart; and opening the pericardial sac to achieve direct access to the heart.

Next, a blood vessel or vessels for use in the graft procedure are mobilized from the patient. This usually entails mobilizing either a mammary artery or a saphenous vein, although other graft vessels may also be used.

Next, a heart-lung or cardiopulmonary bypass is performed. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations.

Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

One area which may create difficulties for the patient and extra expense and time for the procedure involves the cardiopulmonary bypass. In a cardiopulmonary bypass all the patient's blood, which normally returns to the right atrium, is diverted to a system which supplies oxygen to the blood and removes carbon dioxide and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1–9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (February 1993) pgs. 486–489 also reported immobilizing the area of the bypass graft with stabilization sutures.

Current beating heart bypass surgery techniques demand relatively motionless epicardial tissue in the immediate vicinity of an anastomosis. Several systems are presently available which attempt to immobilize epicardial tissue in the immediate vicinity of an anastomosis through a simple mechanical fork. One of the many such systems presently available includes the Access™ system available from CardioThoracic Systems Inc., Cupertino, Calif. Such a system stabilizes the heart by pressing a fork downwards onto the heart surface. Through this pressure the region of the epicardium between the fork is immobilized. Commercially available systems use short arms mounted to retractors in close proximity to the chest cavity. Mechanical fork systems only operate successfully on vessels that can be immobilized by applying pressure in a downward direction. These systems are very useful for operations on the anterior portion of the heart (such as the left anterior descending artery). However, fork systems are limited in their ability to maneuver a vessel into better view or for operating on the posterior portion of the heart. That is, fork systems are limited in their ability to "present" a vessel to the surgeon. This is a even greater drawback since fork systems stabilize only through compression, therefore often pushing downwards the are of surgical interest. In addition, compression of the heart can lead to diminished cardiac output, presenting a further risk to the patient's well-being. Finally, such systems, to date, have often featured rigid, inflexible arms which often interfere with the view or movements or both of the surgeon.

Suction stabilization systems, such as the Medtronic Octopus® Tissue Stabilizer and Accessories (available from Medtronic, Inc., Minneapolis, Minn. USA), use comparatively long dual reusable articulating arms configured with clamps at their distal ends to secure suction based tissue stabilizers. During use, the arms are typically secured to a rail on the side of the operating table. The suction grips and immobilizes the surface of the heart. Additionally, the system allows the surgeon to manipulate the anastomosis site into better view by rotating and supporting the heart. The system also allows the surgeon to apply tension to the tissue between the stabilizers. Thus, the system, is much more versatile than mechanical fork style systems. The suction paddles or pods can attach to and immobilize the heart, and can be used to manipulate the heart into better position so that the more difficult to reach vessels can be bypassed.

Many surgeons have used the Medtronic Octopus® Tissue Stabilizer system to perform as many as five or six vessel bypasses. Some surgeons, in fact, report using the product on 50–90% of their cases. Nonetheless such a system is still in need of improvement. For example, such a system was relatively more cumbersome to set up than desired, requiring each stabilization arm to be individually fixed or immobilized. Moreover, because each arm worked individually, spreading the arms relatively apart was more difficult than desired. Finally, because the degree of spreading was not limited in any way, surgeons could spread the paddles apart at greater distance than desired, causing one or both paddles to spontaneously lose capture of the tissue.

While these past products and attempts have achieved some success, their still exists a need to provide a method and apparatus for performing beating heart surgery which readily and quickly permits the immobilization or stabilization of a local area of tissue.

The present invention concerns an advanced system for immobilizing or stabilizing a local area of tissue.

SUMMARY OF THE INVENTION

The invention is a method and apparatus for performing beating heart surgery, in which a single articulating arm supports multiple suction paddles of pods. Once the suction pods are applied to the heart surface, tightening a cable fixes the arm in place. Then, the suction pods may be spread apart from each other to tighten the surface of the cardiac tissue lying between the suction pods. In one embodiment, fixation of the arm as well as the spreading apart of the suction pods may occur concurrently or almost concurrently through the tensioning of a single cable. Additional embodiments of the method, system and its components are shown.

BRIEF DESCRIPTION OF THE DRAWINGS

The foregoing and other aspects of the present invention will best be appreciated with reference to the detailed description of the invention in conjunction with the accompanying drawings, wherein:

FIGS. 1A through 1F show various views of the invention.

Figure 1B:
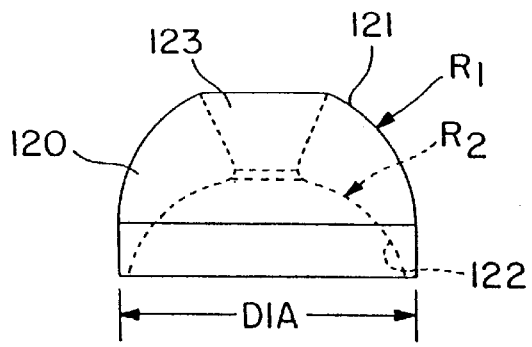

The FIGS. are not necessarily to scale.

DETAILED DESCRIPTION OF THE PRESENT INVENTION

The present invention is a method and apparatus for performing beating heart surgery, in which a single articulating arm supports multiple suction pods or other pods which may be used to grip or engage heart tissue and thus inhibit its motion. In one embodiment, once the suction pods are applied to the heart surface, tightening a cable fixes the arm in place. Then, the suction pods may be spread apart from each other to tighten the surface of the cardiac tissue lying between the suction pods. In one embodiment, fixation of the arm as well as the spreading apart of the suction pods may occur concurrently or almost concurrently the tensioning of a single cable. Additional embodiments of the system and its components are shown. Support for conventional aspects of the invention may be found in the enclosed documents, all of which are incorporated by reference in their entirety.

U.S. Pat. No. 5,727,569 (Benetti et al.)
U.S. Pat. No. 5,782,746 (Wright)
WO 95/01757 (Borst)
WO 97/10753 (Borst et al.)

Preferred embodiments of the invention are shown in the enclosed FIGS., and are described in detail below.

FIG. 1A is a perspective view of a preferred embodiment of the invention. An articulating arm 20 is attached to support 24 on the proximal end of the arm, and terminates with tightening/spreading mechanism 21 at the distal end of the arm. On the opposite, more proximal, end of support 24 is handle 23. Distally beyond tightening/spreading mechanism 21 is a plurality (as shown, two) of suction paddles or pods 22, generally disposed along the same plane. Each suction pod 22 can be connected to a suction source or vacuum (Shown in FIG. 2) by a conventional connection 325 that lies at the proximal end of pod 22. Each pod and its suction ports disposed along the bottom surfaces 1 may be shaped and constructed in any acceptable manner, such as the same as those used in the Medtronic Octopus® tissue stabilizer. Clamp 26 lies below support 24 and is designed to attach the entire device to conventional surgical retractors and other similar equipment (not shown). The preferred embodiment shown in FIG. 1A is illustrative but not intended to be limiting insofar as the scope of the invention is concerned. For example, the handle 23 is shown in a preferred and highly stylized embodiment, but any device which performs the functions of the handle as described below would suffice.

Articulating arm 20 comprises a plurality of "ball and socket" links. FIG. 1B is a cross sectional view of a link used in the arm of the present invention. As seen, each link 120 has a hole 123 that passes through its center. Each link 120 comprises, on its distal end, a hemispherical protrusion 121; and on its proximal end, a hemispherical indentation 122. The hemispherical shapes of adjacent links are nearly identical, such that the links rotate smoothly against one another provided they are not under undue tension with each other.

Figure 1C:
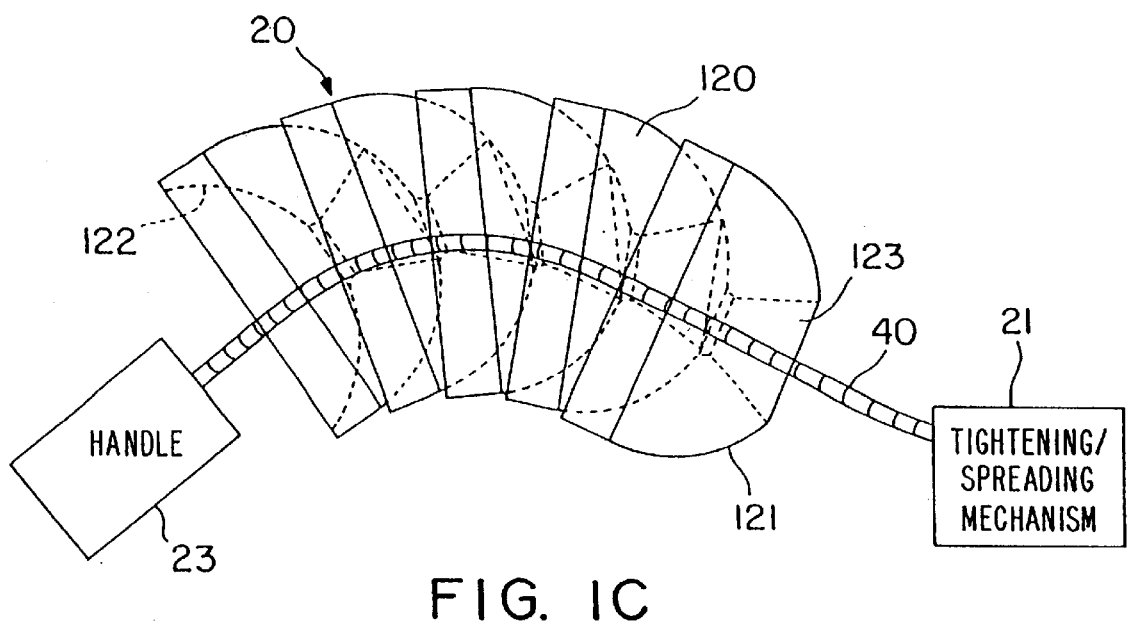

Turning now to FIG. 1C which is a partial view of a section of the links and cable showing the engagement of the cable with the side wall of the links as the arm is bent. A cable 40 passes through hole of all of the links and is connected between the handle 23 and the tightening/spreading mechanism 21. Rotation of handle 23 tightens the cable and causes the links to hold against each other in place. Immobilization of the links relative to each other during tightening of the cable is facilitated by the shape of the hole 123. As seen, hole is flared, having a larger opening with the surface of the hemispherical protrusion 121 and a smaller opening through the surface of the hemispherical indentation 122 The links, as seen in FIG. 1A, vary in size along the length of the arm, with the links in the most proximal portion of the arm being largest, the links in the most proximal portion the smallest and the middle portion somewhere in between. In the preferred embodiment the links have the following outer diameters and radius of curvature for the hemispherical protrusion and radius of curvature for the hemispherical indentation along each of these portions as follows:

| Portion of arm | $R_1$ (inches) | $R_2$ (inches) | DIA (inches) |
| --- | --- | --- | --- |
| Most distal portion | 0.251 | 0.250 | 0.514 |
| Middle portion | 0.313 | 0.311 | 0.637 |
| Most proximal portion | 0.317 | 0.374 | 0.763 |

The above dimensions are exemplary and other dimension may also be selected. In the preferred embodiment, the links are fabricated out of highly rigid engineered thermoplastics such as glass filled Ultem™ (available from GE Plastics, Pittsfield, Mass.) Preferably the highly rigid engineered thermoplastics includes at least 20% glass fiber, and better still at least 30% glass fiber. This material offers stiffness comparable to metal systems, and yet can be manufactured at costs that allow for single use disposability. The cable is preferably a multi-stranded stainless steel cable having between approximately 7 to 19 strands. The links and cable may also be manufactured from other materials, including any other suitable highly engineered polymers including any number of available liquid crystal polymers for the links, as well as many other types of cables, including bundle stranded, braided or cabled titanium as well as Kevlar™ for the cable.

The preferred embodiment also employs a textured surface molded or otherwise formed into the hemispherical features of the links. When the links are pulled together during tightening, the texturing causes an increase in coefficient of friction between the adjacent spherical surfaces. This has the highly desirable benefit of increasing overall system stiffness. This is depicted in FIG. 1D. Which depicts the roughened surfaces between the ball and socket, such that in tension, the elements are more securely linked together. As seen, in the preferred embodiment, the texture provided is irregular, that is, the texture is non-uniform, and has an average height spanning approximately (peak to valley) of between 20 to 100 microns, with an average height (height$_{avg}$) spanning approximately 40 microns preferred. As seen in FIG. 1E, moreover, in an alternative embodiment texture may be provided through a symmetrical structure, depicted here as a series of interlocking dimples 127 and hemispheres 128. Other geometries may also be used, including both surface having the same elements, such as hemispheres, as well as other shapes, including notches or grooves, to name only a few.

In this embodiment, articulating arm links 120 have a decreasing outer diameter from the proximal portion to distal end portion of the arm. This is also seen in FIG. 1A, where outer diameter of the most proximal link portion $D_{MPL}$ is larger is that the outer diameter of the middle link portion $D_{MLP}$ which, in turn, is larger is that the outer diameter of the most distal link portion $D_{MDL}$. Decreasing the link diameter allows a lower profile assembly that improves the ability of the surgeon to use the device without unduly restricting accessibility to the surgical site while further ensuring adequate rigidity. In the preferred embodiment $D_{MPL}$ is approximately 0.75 inches, $D_{MDL}$ is approximately 0.50 inches and the $D_{MLP}$ a outer diameter of approximately 0.625 inches, and the total arm length is approximately 10.25 inches with the pods and approximately 9 inches without the pods. Further, in the preferred embodiment most proximal link portion features 19 links, middle link portion features 4 links, and most distal link portion features 3 links.

Figure 1F:
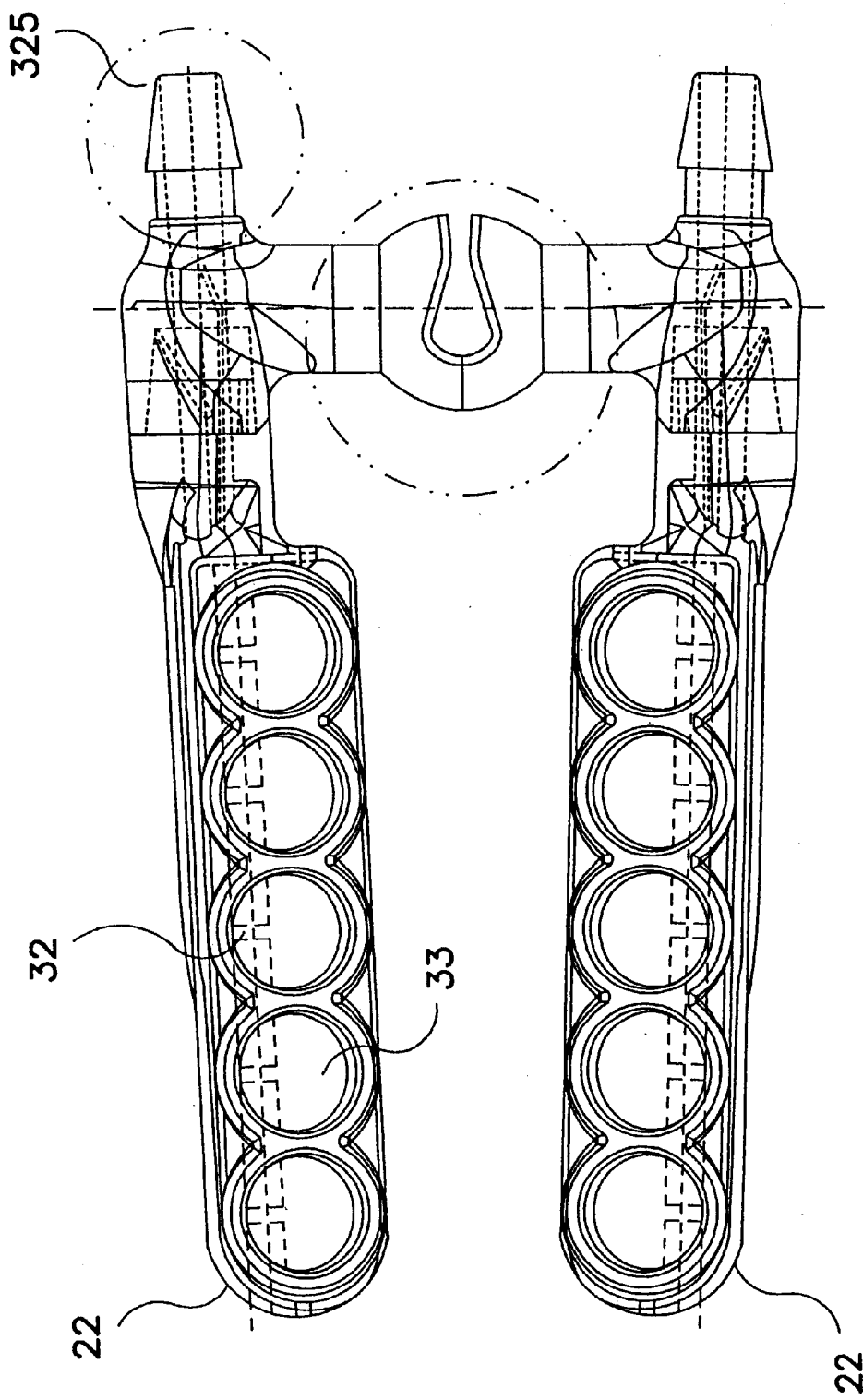

FIG. 1F is a view of the bottom of the suction pods 22. As seen, in the preferred embodiment four suction ports 133 in a row are featured, although the specific or exact number and position used may vary. Each suction port 133 has a suction aperture 132, each of which are preferably located at a position off-center from suction port 133. Suction apertures 132 are positioned off center from suction ports 133 so that if a large upwelling of tissue is caused by the suction (which may occur as a blister or bell-shaped curve) the tissue will not immediately close off the suction by obstructing suction aperture 132, as it would if the aperture were in the center of suction port 133. In addition, each suction aperture 132 has a much smaller opening surface area diameter as compared to the diameter of suction port 133. This creates a high resistance pathway between suction port 133 and suction conduit 131 which permits the loss of a tissue-to-port seal in one suction port (and thus loss of fixation of the suction port to the tissue) to not also cause a precipitous pressure drop in the remainder of the suction ports. In the preferred embodiment suction port 133 has a diameter of 6 mm, while each suction aperture 132 has a opening surface area of approx 3 sq. mm. Each suction port, moreover, is generally straight sided. The above dimensions are exemplary and other dimension may also be selected.

Figure 2:
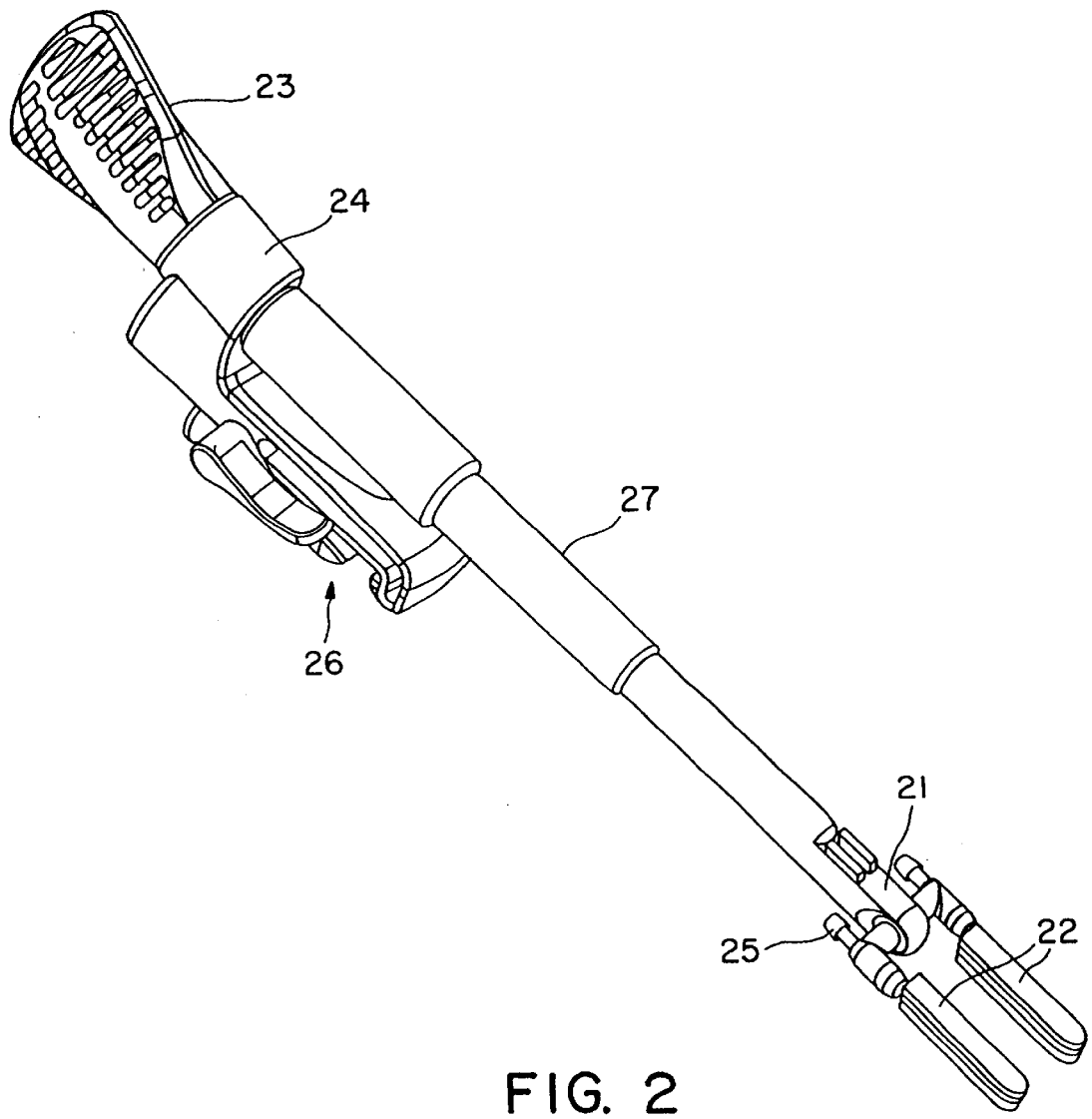
FIG. 2 is an alternate embodiment of the present invention.

In an alternate embodiment, as shown in FIG. 2, the links of articulating arm 20 are covered with a thin walled elastomeric sheath 27. The sheath serves to prevent fragile sutures from catching on the edges where the links join. Sheath is preferably manufactured of silicone rubber, although other materials, such as latex rubber or polyurethane or even collagen, may also be used.

Figure 3:
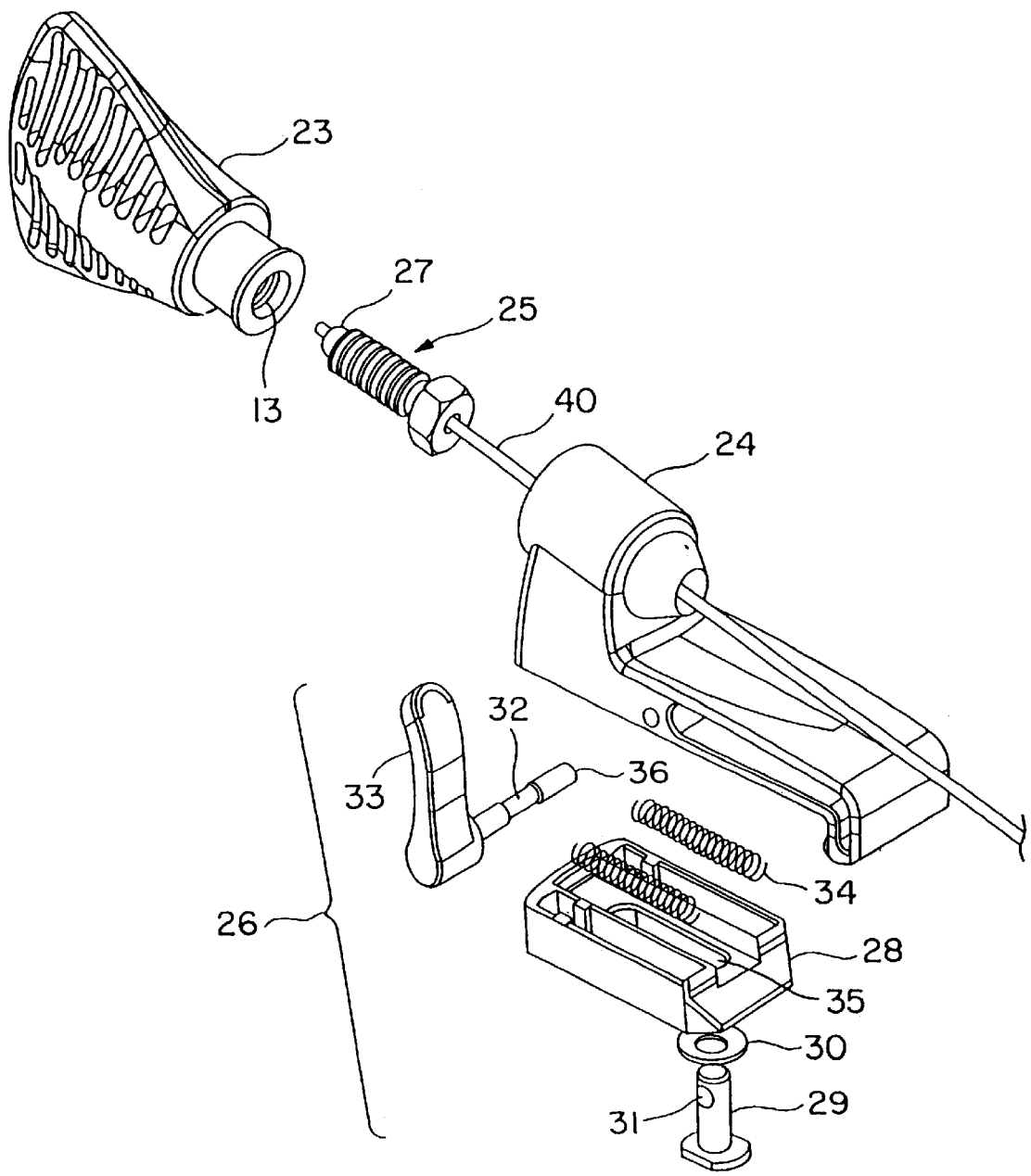
FIG. 3 is an exploded perspective view of the cable tensioning and device clamping mechanisms.

FIG. 3 is an exploded perspective view of the cable tensioning and device clamping mechanisms. Tension is applied to cable 40 by a torque screw and nut configuration at the proximal end of the device. Cable 40 passes through mount 24, and then through the bore of torque screw 25, and terminates in a swaged connector 27. In the preferred embodiment shown, the torque screw interacts with a corresponding nut portion 13 which is integrally formed within handle 23, although an embodiment in which handle 23 turned a separate nut is within the scope of the invention. Torques screw preferably is threaded at 12 threads per inch. As handle 23 is rotated, torque screw 25 engages nut portion 13 and advances proximally into handle 23, tensioning cable 40. It is preferred, for safety purposes, for the degree or amount of cable tensioning in the system to be limited. In the preferred embodiment this is accomplished by sizing housing 24, torque screw 25, and handle 23 such that torque screw 25 may advance into handle 23 along nut portion only a predetermined amount. In such a manner the system is configured so that the cable may not be over-tensioned, i.e., tightening of cable 40 is limited so as to remain comfortably below the rated strength of cable 40.

The torque screw, through the mechanical advantage of a 12 thread per inch torque screw allows cable tensions as high as 500 lb. to be applied by hand. While the actuation is somewhat slower than possible other type actuators (e.g. scissors-type actuator) the high tension in the cable optimizes arm rigidity.

Arm rigidity is further enhanced through the interplay between the multi-stranded cable riding on the inner diameter of the plastic segments. The multi-stranded cable riding on the inner diameter of the plastic segments induces additional friction which optimizes stability. As the cable is tensioned at high load values (>200 lb.), the cable digs into the inner diameter of the softer plastic of the segments. This is depicted above in regards to FIG. 1C which is a partial view of a section of the links and cable showing the engagement of the cable with the side wall of the links as the arm is bent. Since the cable is striated with typically 7–19 strands, the result is a strong interlocking of cable and plastic segments. The interlocking of the stranded cable to the plastic segment increases the coefficient of friction between cable and plastic segment. This further locks up segments to each other since they cannot slide easily along the cable. Thus enhancing arm rigidity. Below sufficient cable tension, however, the cable does not dig into the links and cause the strong increase in coefficient of friction. Additional embodiments of the invention may also feature cables of greater surface roughness, as well as sheathing the cable in materials sheaths having a greater coefficient of friction than the cable itself. Such friction enhance sheaths are particularly believed useful where cables other than stranded cables are used, such as Kevlar™ cables, as mentioned above.

The complete device is designed to be clamped to a wide variety of commonly used sternal retractors. Clamping mechanism 26 comprises mating portions of mount 24 and a movable jaw 28, each configured to provide half of a dovetail shaped groove. Movable jaw 28 is attached to mount 24 by a center pin 29 that passes through a groove 28 in the movable jaw 28. Center pin 29 also passes through conical spring washer 30. Groove 35 allows movable jaw 28 slide back and forth, permitting mounting to retractor elements of varying width. Center pin 29 comprises a cross hole 31. A Cam pin 36, which is rigidly affixed to a knob 33, passes through cross hole 31, capturing together the movable jaw 28 and the mount 24. Cam pin 36 has an off-axis lobe 32 which induces upward movement on center pin 29 when knob 33 is advanced forward (in the FIG. 3, clockwise) to a horizontal position parallel to the cable 40. This upward motion compresses spring washer 30, which pulls the two halves of the clamp together. This induces, onto the retractor, both horizontal and vertical clamping forces in the dovetail features of the clamp halves, securing the clamp in place. Movable jaw 28 is additionally provided with dual compression springs 34 which bias the clamp to a fully forward position. This provides more convenient mounting of the clamp, and also ensures a more reliable connection between the mount and retractor element.

Figure 4:
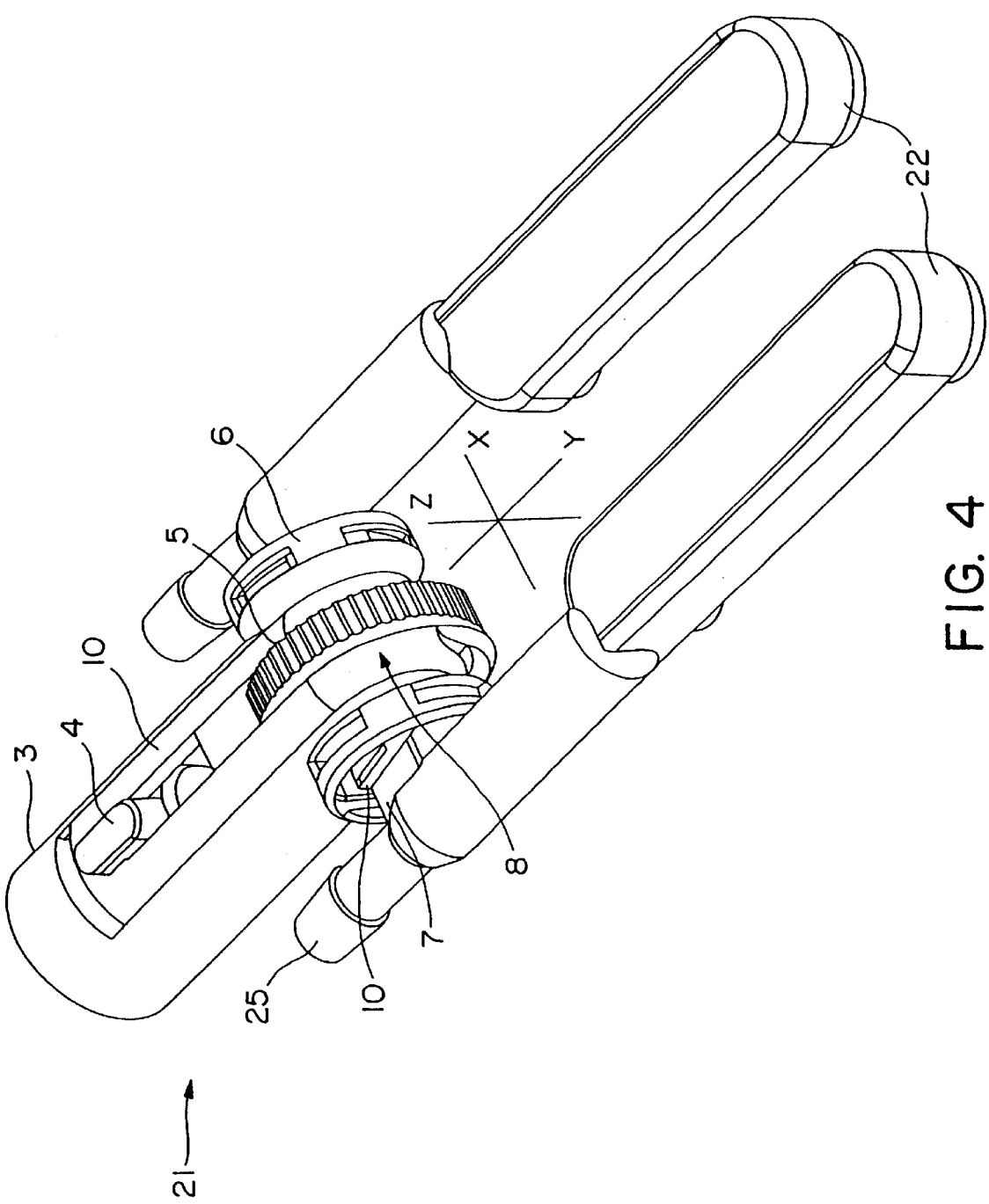
FIG. 4 is a perspective view of the first of three preferred embodiments for tightening/spreading mechanism 21.
Figure 5:
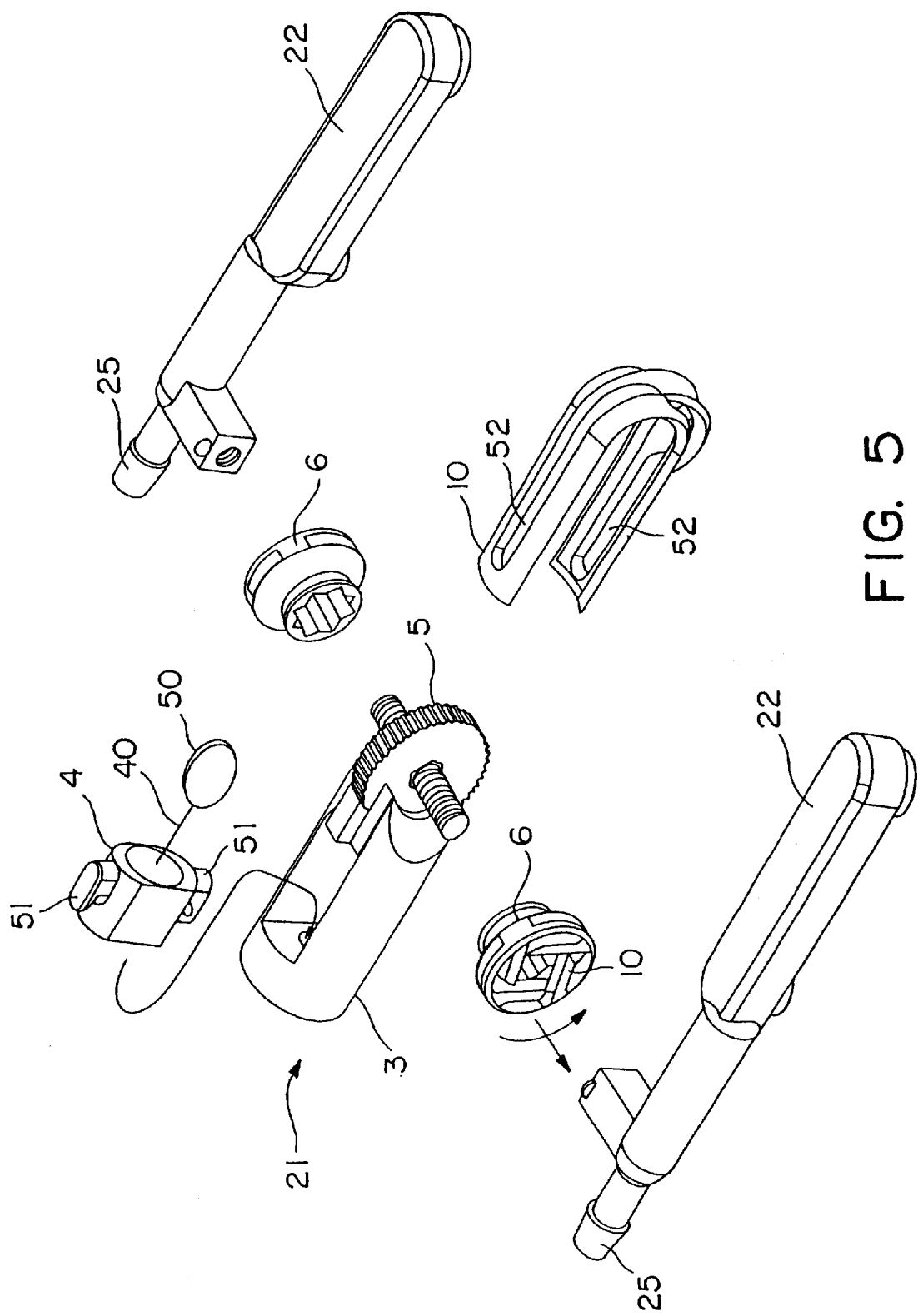
FIG. 5 is an exploded perspective view of the tightening components of FIG. 4.

FIG. 4 is a perspective view of the first of three preferred embodiments for tightening/spreading mechanism 21. FIG. 5 is an exploded perspective view of the tightening components of FIG. 4. The embodiment of FIGS. 4 and 5 provides simultaneous parallel translation of suction pods 22, along the x-axis, by rotation of wheel 5. This spreading/closing action can be performed when the articulating arm 20 is either loose or tight. Additionally, when articulating arm 20 is loose, suction pods 22 can be independently rotated about the yz plane. This allows the surgeon wide flexibility in the manner of approach to the anastomosis site. Because the spreading action is parallel, the cardiac tissue tensioning effect is uniform across the anastomosis site (below and between suction pods 22). Of course, although shown here as parallel, the paddles or pods may also be disposed, if desired, in a non-parallel orientation on the distal end of arm, if desired by the surgeon.

Cable 40 terminates at tabbed element 4 by cable ball 50. Tensioning of cable 40 causes tabbed element 4 to move proximally. Ears 51 of tab element 4 mate into slot 52 of sling 10. Thus, tensioning or pulling on cable imparts tension or pulling back on sling 10. Sling 10 wraps around two pod guides 6, capturing guides 6 against head link 3. As cable 40 is tightened, sling 10 pulls pod guides 6 ever more firmly into head link 3 until they can no longer rotate. In the preferred embodiment, pod guides 6 are configured with square holes. These square holes are provided to mate with square projections on the pod guides and thus guide the movement of suction pods 22 in and out. The square shape serves to prevent rotation of suction pods 22 in the yz plane once cable 40 has been tightened. Additionally, to prevent minor oscillations of suction pods 22 in the yz plane due to small clearances between pod guides 6 and suction pods 22, pod guides 6 each include small torsion springs 10 which bias suction pods 22 to one side of the respective pod guide 6. Suction pods 22 have a square element, which projects into the center of the spreader mechanism through pod guides 6.

Wheel 5 is located between the two pod guides 6. Wheel 5 has a threaded rod projecting through its center along the x-axis. To one side of wheel 5, the threaded rod has a right hand thread, and to the other side, a left hand thread. These threads mate with respectively threaded holes in the projections of the two suction pods 22. Rotating wheel 5 causes the pods to move simultaneously apart or together. Vacuum connections to suction pods 22 are made via barbed connections 325 at the proximal end of suction pods 22. Still further, this embodiment may be modified through the provision of two wheels, the rotation of one controls the movement of the first pod, while the rotation of the other controls the rotation of the second pod. In such a manner the pods may be configured to be independently moveable relative to each other. Even still further, only one of the two pods may be provided for movement so that the first pod remains fixed while the second pod is moved through rotation of the wheel. Moreover, any of the above embodiments may be provided wherein the pods are initially disposed in either a parallel or an angled orientation relative to each other, as shown below. Further still, any combination of one or more pods being moveable, as well as angled relative to one another may be provided, if desired by the surgeon.

Figure 6:
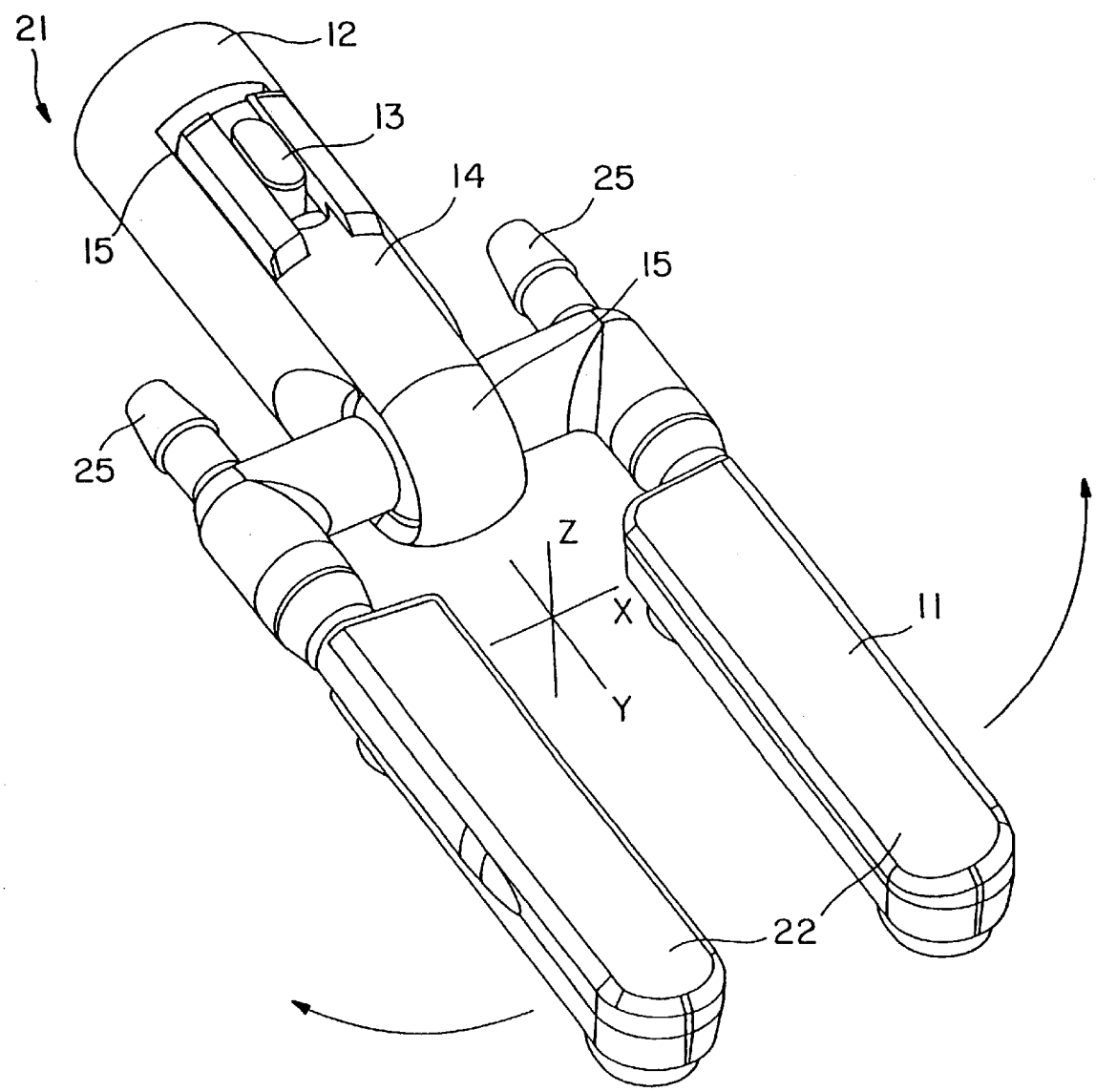
FIG. 6 is a perspective view of the second of three preferred embodiments for tightening/spreading mechanism 21.
Figure 7:
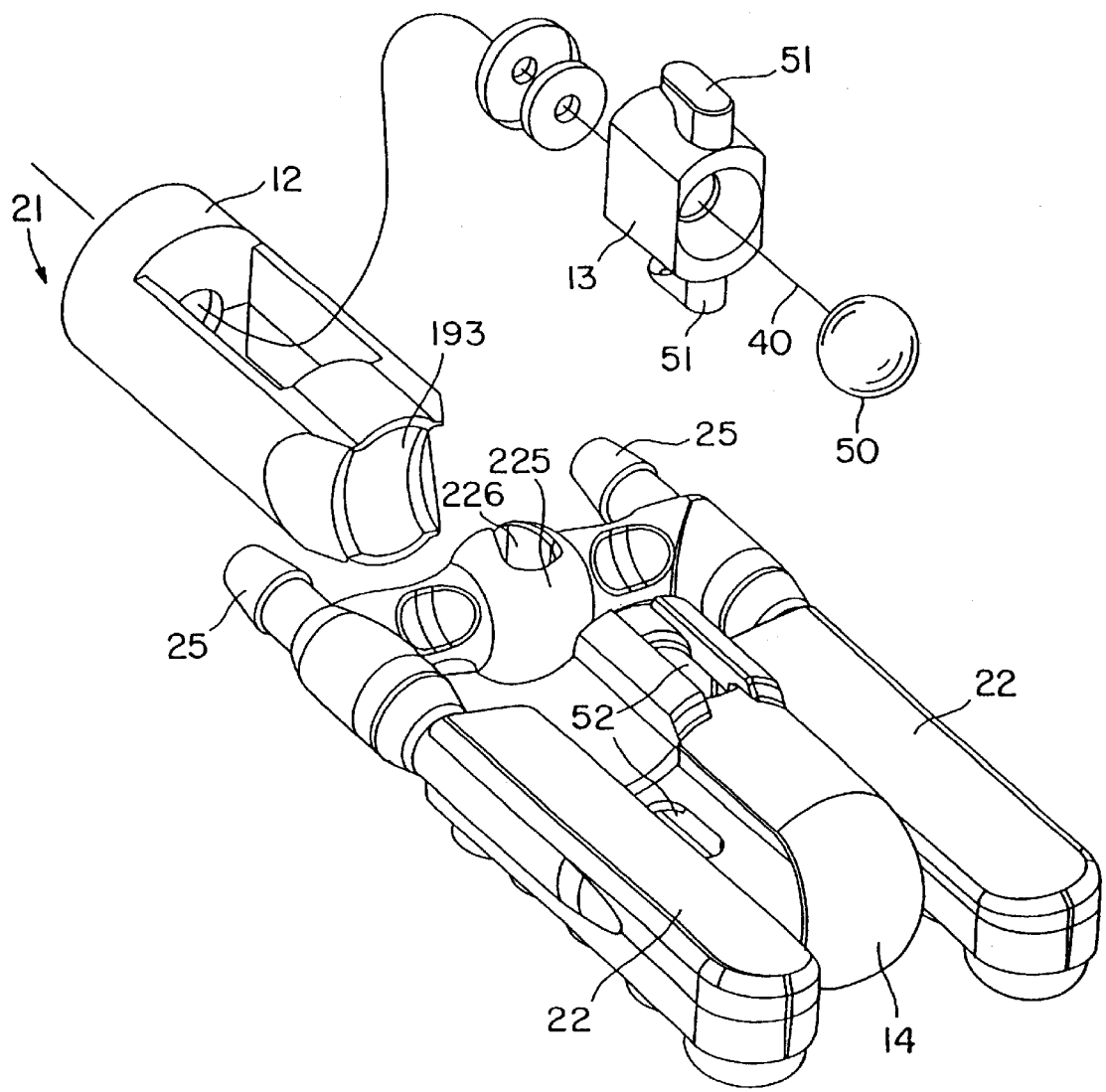
FIG. 7 is an exploded perspective view of the tightening components of FIG. 6.

FIG. 6 is a perspective view of the second of three preferred embodiments for tightening/spreading mechanism 21. FIG. 7 is an exploded perspective view of the tightening components of FIG. 6. The embodiment of FIGS. 6 and 7 provides sequential tightening of the articulating arm concurrently or closely followed by angular separation of suction pods 22 in the xy plane, by tightening of handle 23. When articulating arm 20 is loose, suction pods 22 are free to rotate in the yz plane, and to a lesser extent in the xz and xy planes. This allows the surgeon even greater flexibility on approaching the anastomosis site. The tightening of cable 40 causes the spreading action. Because the spreading action is rotational, the tensioning effect will be uneven, being generally V-shaped, that is more pronounced at the distal end of the anastomosis site.

Cable 40 terminates in tabbed element 13. Tensioning of the cable causes the tabbed element to move proximally, pulling back on sling 14. The sling wraps around the split ball 225 of pods, capturing the split ball. In its relaxed state, when the stainless cable is loose, relatively little friction exist between split ball 225, inner cavity of sling 14 and outer spherical surface of head link 12 so that split ball 225 is relatively able to be moved or rotated therein. In the preferred embodiment, the outside diameter of split ball is equal to the diameter of that spherical cavity defined within sling and head link, preferably these diameters are all approximately 0.193 inches. As the cable is tightened, however, the sling cinches down over the split ball compressing the split ball into the sling and head link 12. As the split ball 225 is compressed, the split 226 closes, causing suction pods 22 to splay angularly outward. In the preferred embodiment split ball 225 is made from non-glassed filled Ultem™ (available from GE Plastics, Pittsfield, Mass.)

In a preferred embodiment, a compressible (preferably elastomeric) disk 15, is mounted between sling 14 and head link 12. The preferred material for disk 15 is silicone with a durometer of 80, although other materials or durometers or both may also be selected. Disk 15 preferably sits or mates into a compression limiter 41, depicted here as a stainless steel cup 41, which functions to limit the total amount to which the disk may be compressed. That is, disk 15 is sized to fit within cup so as to be able to be compressed an amount no greater than the depth of the cup. In the preferred embodiment, allowed to be compressed approximately no more than 0.040 inches. Of course, other sizes and material may also be selected. The identity, size, and other materials properties of the elastomeric disk 15 and cup (if used, for example, cup could be integrated into head link or cable tab) are chosen such that disk 15 it is crushed between head link 12 and sling 14 before the split ball is compressed. This causes articulating arm 20 to become firm before the spreading or other moving of the suction pods 22 begins, adding a desired degree of control to the system. Vacuum connections to suction pods 22 are made via barbed connections 325 at the proximal end of suction pods 22.

Figure 8:
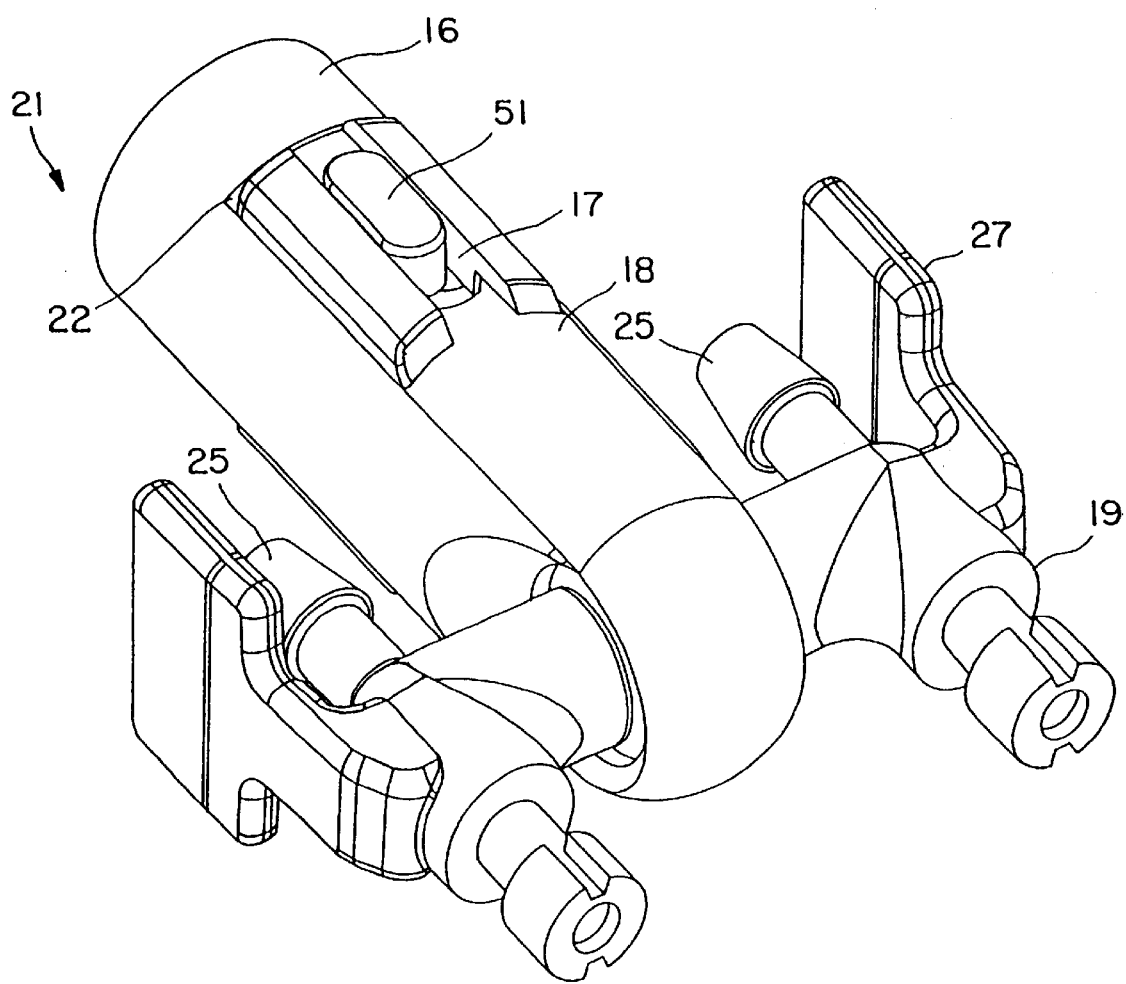
FIG. 8 is a perspective view of the third of three preferred embodiments for tightening/spreading mechanism 21.
Figure 9:
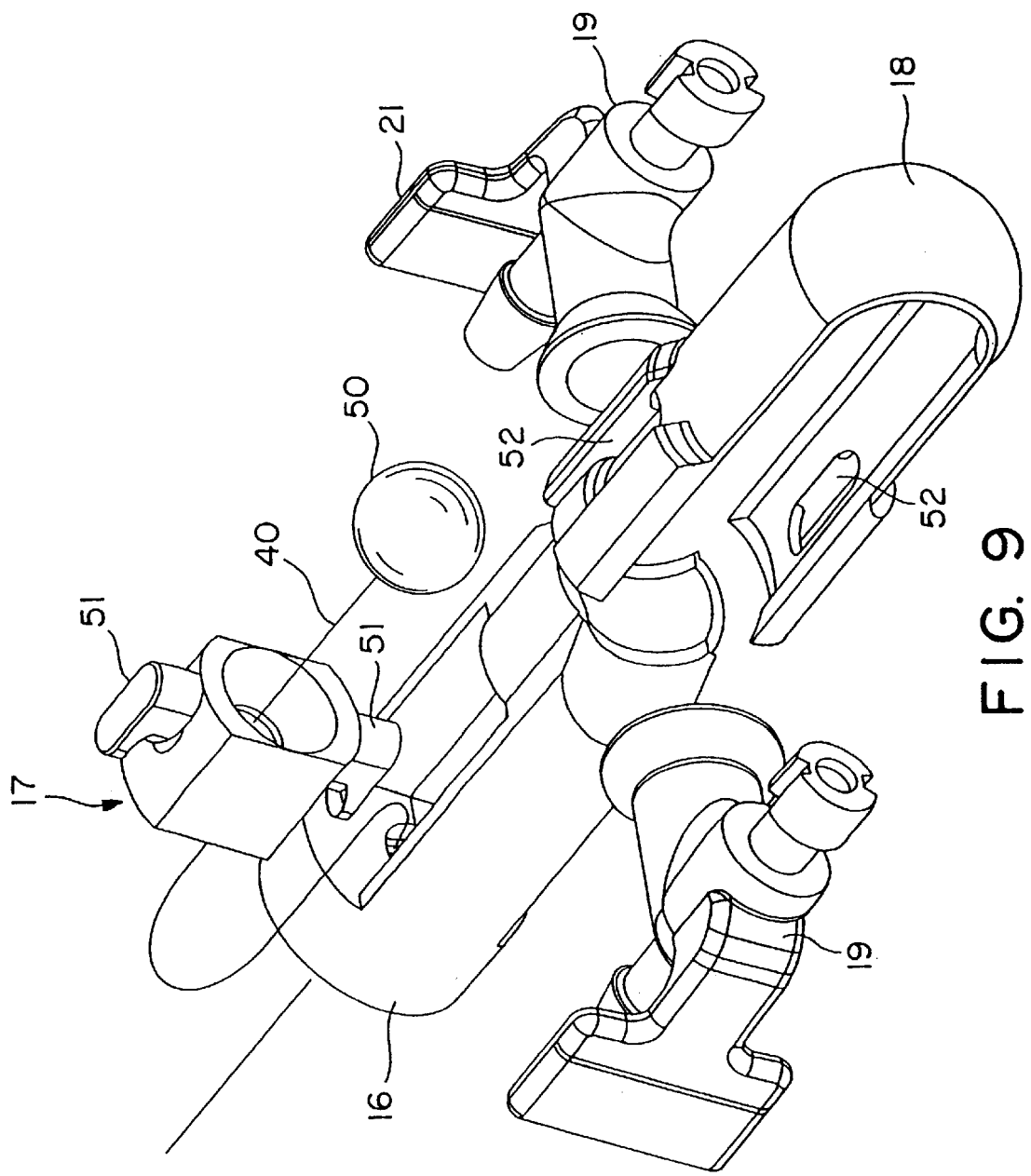
FIG. 9 is an exploded perspective view of the tightening components of FIG. 8.

FIG. 8 is a perspective view of the third of three preferred embodiments for tightening/spreading mechanism 21. FIG. 9 is an exploded perspective view of the tightening components of FIG. 8. The embodiment of FIGS. 8 and 9 provides independent rotational spreading of the suction pods (not shown in these two FIGS.) in any plane about a point of rotation at the center of the mechanism. When articulating arm 20 is loose, the suction pods 22 will move freely. Because the suction pods 22 are not linked together in this embodiment, they are able to conform to surfaces of the heart where the suction pods would not be co-planar. This provides more secure mounting of the suction pods on areas of the heart with small radii of surface curvature.

Cable 40 terminates at tabbed element 17. Tensioning of the cable causes tabbed element 17 to move proximally, pulling back on sling 18 through the interaction of ears 51 and groove 52. Pod mounts 19 each contain hemispherical sockets that fit smoothly about ball 50 and are captured between sling 18 and head link 16. Tensioning of cable 40 causes tabbed element 17 to move proximally, pulling back on sling 18, pinching ball 50 and the pod elements firmly together. In use, the surgeon would partially tighten the cable, and then pinch together the pod finger tabs 27 to achieve the desired a amount of spreading. In a preferred embodiment, a compressible disk is used as described previously. Vacuum connections to the suction pods are made via barbed connections 25.

Figure 10:
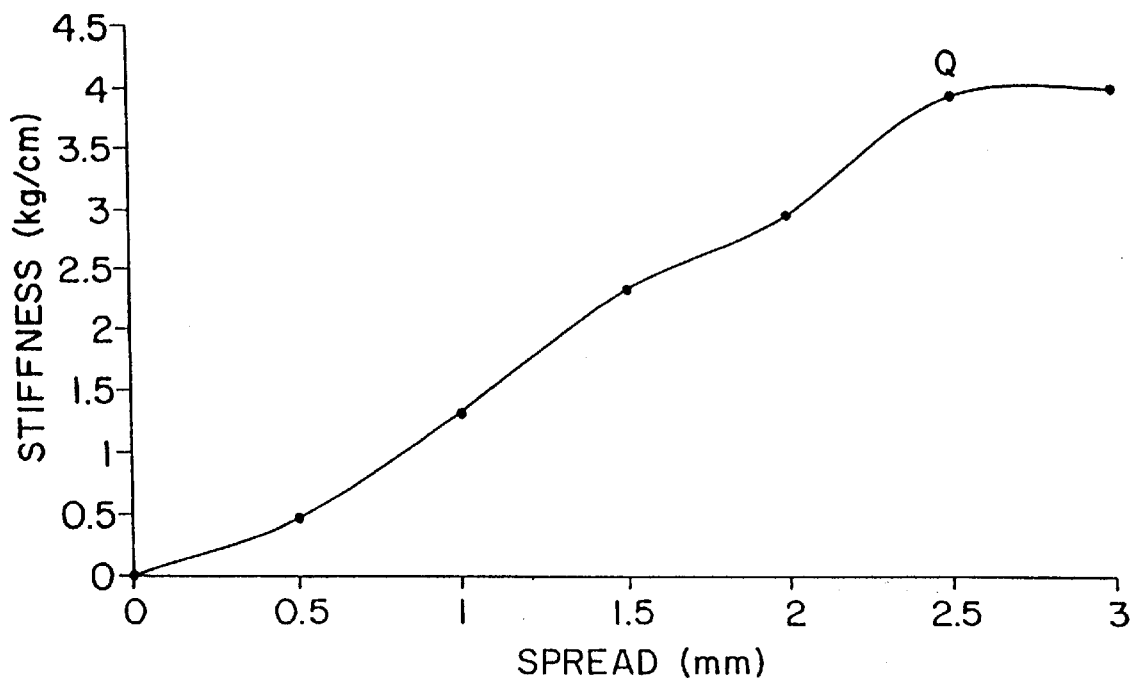
FIGS. 10–45 show additional features and alternative embodiments of the present invention.

FIG. 10 depicts the relationship between rigidity of the articulating arm and the spreading apart of the suction pods 22 shown above in FIG. 1A. As seen the present invention is designed so to provide a particular relationship between the rigidity of articulating arm and the spreading of suction pods. In the embodiment shown in FIGS. 6 & 7 the initial relationship between rigidity and spread is linear until a spreading point, seen here as Q, is reached. Thereafter a non-linear relationship is seen. In this embodiment there is thus a simultaneous change in the rigidity of the arm and the spreading of the pods.

Figure 11:
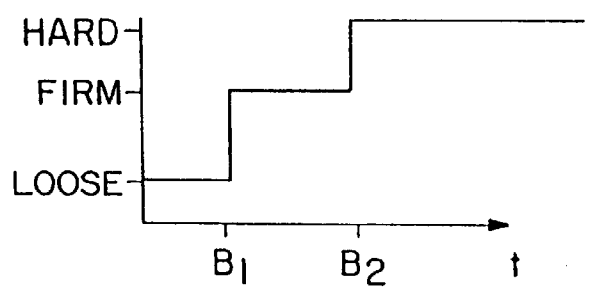
Figure 12:
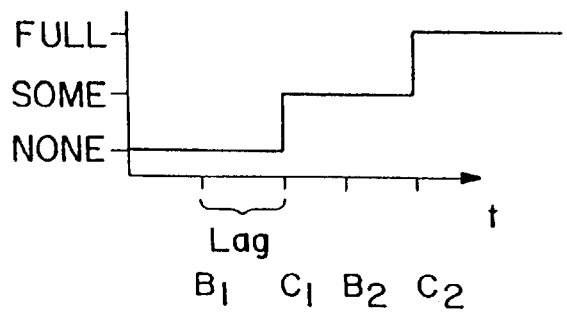

FIGS. 11 & 12 depict the relationship of rigidity and spreadablity in a further embodiment of the present invention. As seen in this embodiment the articulating arm undergoes a transformation of rigidity from loose flexibility to firm flexibility at time $B_1$. Thereafter, at time $B_2$ articulating arm undergoes a transformation of rigidity from firm to hard. Continuing tightening of the handle (which controls rigidity and spread in the embodiment shown in FIGS. 1–7) does not cause the arm to become appreciatively more rigid. In contrast, the spreadability of the suction pods is depicted in FIG. 12 and is seen, in particular, to occur at a lag from the transformation of rigidity. In particular, as seen at $B_1$ the rigidity is increased from loose to firm while the spread of the suction pods does not occur until time $C_1$ that is, turning of handle 23 to reduce the flexibility of the part of the articulating arm from loose to firm does not cause an appreciable spread until a time thereafter, here seen as $C_1$. The particular relation between rigidity and spread may be selected to occur in any favorable matter. Practically speaking, the relationship between rigidity and spread may be a matter of choice which is best left to the surgeon. Thus, the present invention permits this relationship to be tailored as desired though the selection of among the following factors: in the present invention shown in FIG. 1A and thereafter shown in particular regard in FIGS. 6 & 7, the relationship of rigidity and spread may be controlled through the particular design and selection of the arm links and texture, split ball and hinge, split ball and split or gap, washer and cup as well as any of their materials.

Figure 13:
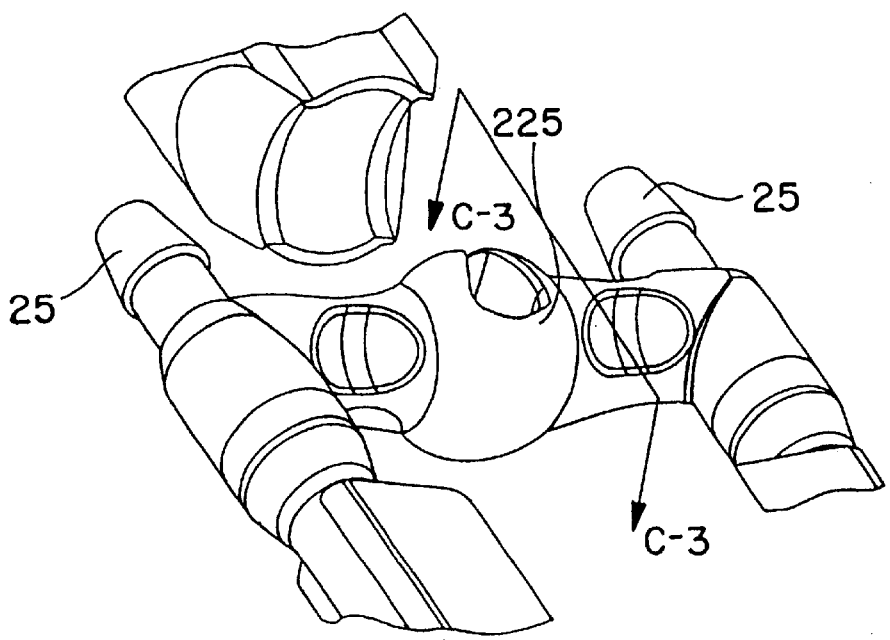
Figures 14, 15:
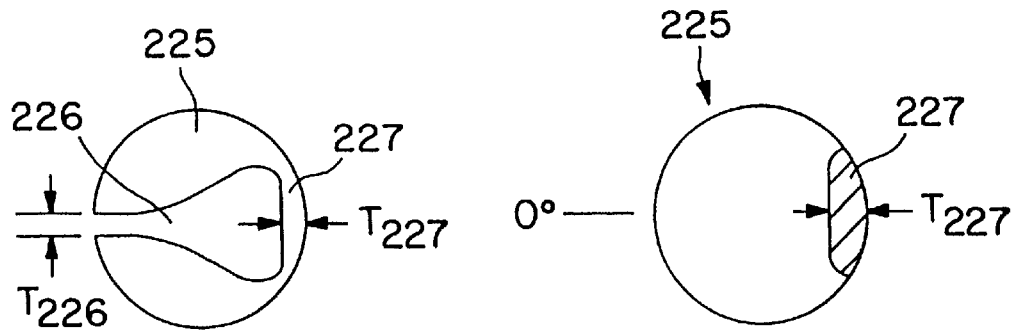
Figure 16:
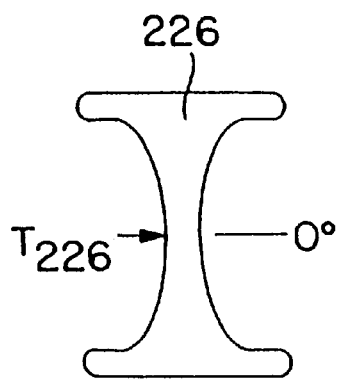

This is seen in FIGS. 13 through 21, which show the split ball 225 of the preferred embodiment (FIGS. 13 through 16) and alternative designs. As seen FIG. 13 is a detailed perspective of split ball 225 shown assembled in a stabilization system. FIG. 14 is a plan view of the split ball 225 shown in FIG. 13 from an overhead position. This view shows the split or gap 226 within split ball and the hinge 227. The size of hinge 227 and split or gap 226 define the actuation of the pods mounted to the split ball and further the degree of force required. These elements, along with other elements of the present invention, may be tailored to provide the particular actuation and performance characteristics deemed suitable for a surgeon or surgeons. FIG. 15 is a cross sectional view of split ball 225 shown in FIG. 13 along line 15—15. In the preferred embodiment gap 226 has a minimum thickness $T_{226}$ of between 0.010–0.100 inches, with 0.040 inches preferred, while hinge 227 has a thickness $T_{227}$ of between 0.220–0.010 inches, with 0.110 inches preferred. FIG. 16 is a two-dimensional plot of the gap along the outer surface of the split ball. As seen, in this embodiment, gap is symmetrical along the outer surface.

Figure 17:
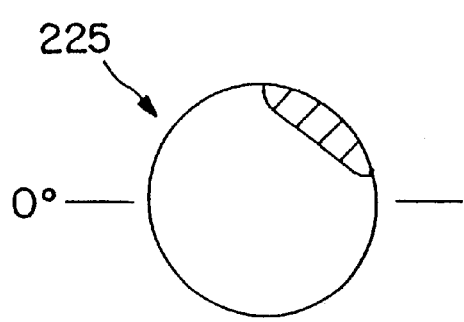
Figure 18:
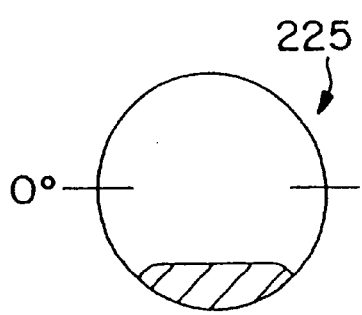
Figure 19:
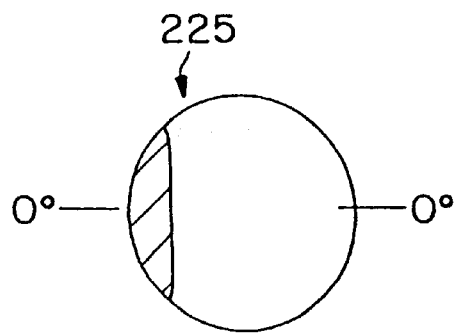
Figure 20:
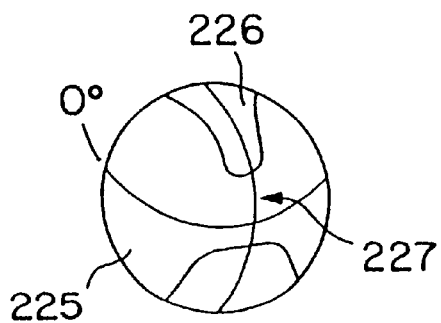
Figure 21:
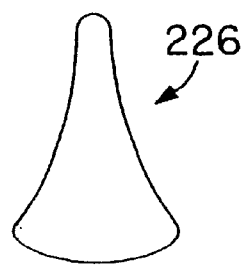

Many other alternative embodiments of the split ball may be provided. FIG. 17 shows one embodiment in which the hinge is positioned above the center line of the split ball. FIG. 18 shows one embodiment in which the hinge is positioned below the center line of the split ball. FIG. 19 shows one embodiment in which the hinge is positioned at the backside of the split ball, as compared to the embodiment seen in FIG. 15. In this embodiment the tension on the cable would cause the front of the spit ball to be compressed, thereby splaying inwardly the suction pods. Such pod movement may be useful for squeezing tissue between the pods. Besides positioning the gap and thus the hinge at various portions within the split ball, gap may further be fashioned so as to be larger at a top end and smaller or narrower at a bottom end. FIG. 20 shows an embodiment in which gap 227 is wider at the upper end (above the 0 degree line) and narrower at the lower end (below the 0 degree line). FIG. 21 is a two-dimensional plot of the gap along the outer surface of the split ball. As seen, in this embodiment, gap is non-symmetrical along the outer surface, larger at its upper end and narrower at its bottom end. This embodiment would tend to cause the paddles to be generally moved apart as well as undergo a slight rotation along each paddle's longitudinal axis. An example of such spreading and rotation motion is shown below. The particular configuration of the split and its orientation along the equator and meridian of the ball may be selected to provide the desired movement.

Figure 22:
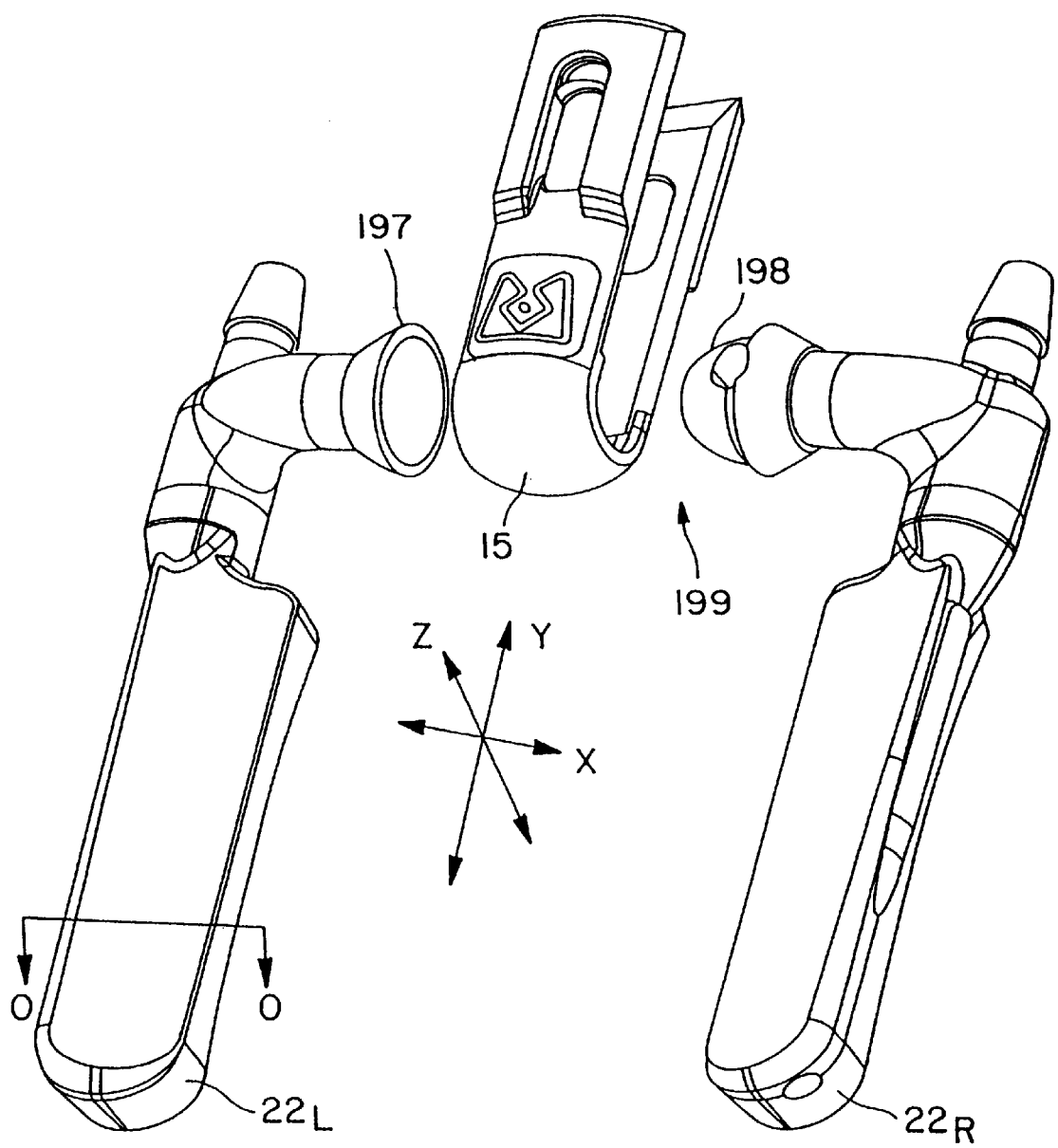

FIG. 22 depicts an alternative embodiment of the present invention. In this embodiment suction pods are separated, and not joined such that each suction pod is free to be moved within the Y Z plane, similar to that already shown in FIG. 4. Movement is provided through the segmented spreadable hinge 199, which is provided through the interrelationship of sling 15 and the corresponding left suction pod 22L and right suction pod 22R. Spreadable hinge 199 is provided through an inter-mating ball and socket assembly, provided on respective floating pods 22R and 22L in particular a hemispherical ball 198 is provided on right suction pod 22R and a corresponding inter-mating hemispherical socket 197. As seen socket and ball are dimensioned such that they may be mated together and the smaller diameter portion of ball inserted into the hemispherical opening of hemispherical socket 197. Thereafter the mated together pieces generally form a segmented hemisphere which may be disposed within the sling 15 as already described above in regards to FIGS. 6 & 7. This embodiment has advantages over that shown above in FIGS. 6 & 7 because the individual paddles 22L & 22R may be oriented along the various axis to provide secure capture of the surface of the heart.

Figure 23:
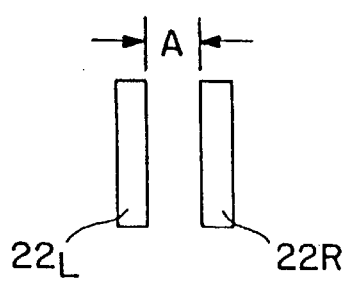
Figure 24:
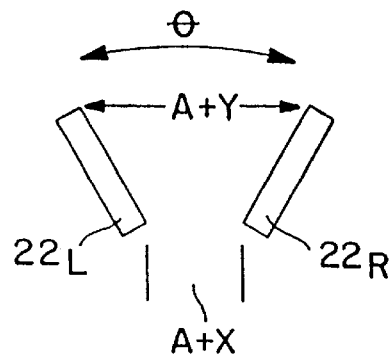
Figure 25:
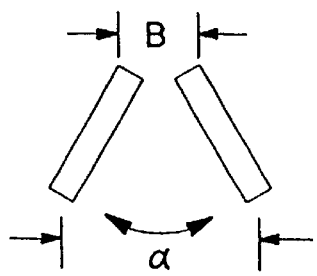
Figure 26:
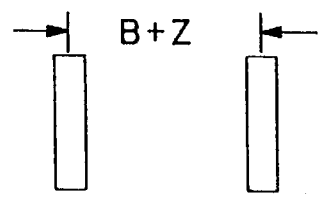
Figure 27:
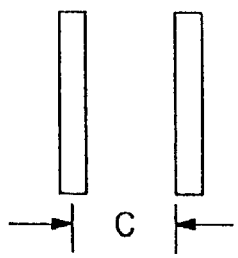
Figure 28:
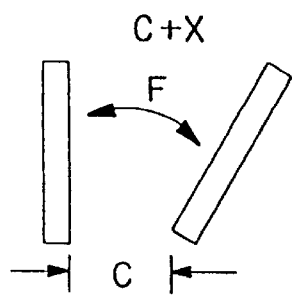
Figure 29:
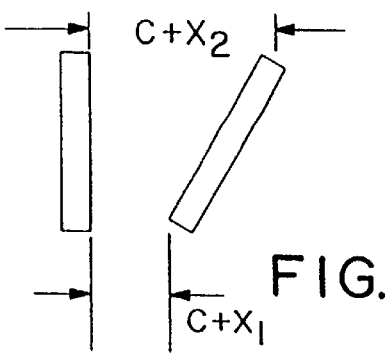

In a further embodiment of the present invention the segmented spreadable hinge 199 as well as spreadable hinge shown above in regards to FIGS. 6 & 7 may be provided such that the suction pods move in a non-parallel fashion. One embodiment of this non-parallel movement is shown in FIG. 23. As seen in a first, non-spread, orientation paddle 22L & 22R are disposed of first distance A apart. Once the spreading has been ignited through any of the various methods described above, paddles 22L & 22R reach the disposition of FIG. 24. As seen in this disposition the closes point the paddles have to one another is at their base or proximal positions and is at a distance A+X. The distal ends of the paddles are shown at a distance A+Y apart such that an angle faded exists between the longitude and the axis of each paddle. Embodiments which may be utilized to achieve such movement are those shown above. Likewise, FIG. 25 shows and additional embodiment in which the paddles start at a disposition where the distal ends are a distance B apart, and disposed at an angle alpha relative to one another. After movement paddles reach tie disposition shown in FIG. 26, and are generally parallel to one another and are now at a distance B+Z apart. Embodiments which may be utilized to achieve such movement are those shown above. Likewise, FIG. 27 shows and additional embodiment in which the paddles start at a disposition where the paddles are a distance C apart. After movement paddles reach the disposition shown in either FIG. 28 or 29, and are generally angled at an angle beta relative to one another, having a distance at the distal end of either C+X or C+$X_2$ and a proximal distance of either C or C+$X_1$. Embodiments which may be utilized to achieve such movement are those shown above.

Figure 30:
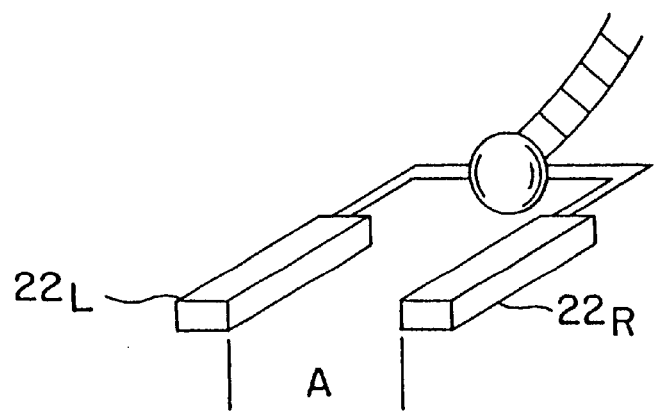
Figure 31:
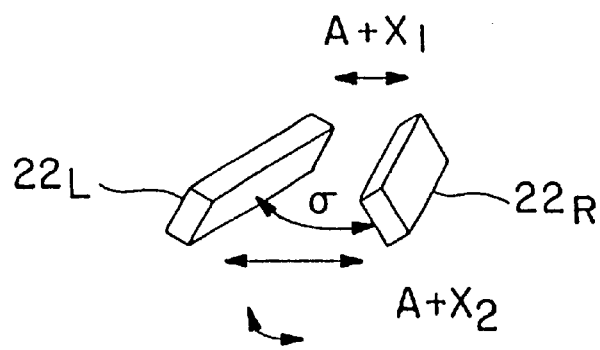

FIG. 30 depicts further alternative embodiment of the present invention. In this embodiment suction pods 22L & 22R may be spread and rotated such that they move from an orientation shown in FIG. 30, and have a distance A apart, to the orientation shown in FIG. 31. As seen in FIG. 31, at this point paddles 22l & 22R are a minimal distance A+X1 apart at their proximal end an greater distance A+X2 apart at their distal end. Furthermore, the pods have had a relative rotation such that the bottom surface of the pods now define an angle sigma. Such movement may be provided through, among other ways, the a split ball having a split which is non-symmetrical across the plane defined by the paddles, such as the split ball shown in FIG. 20.

Figure 32:
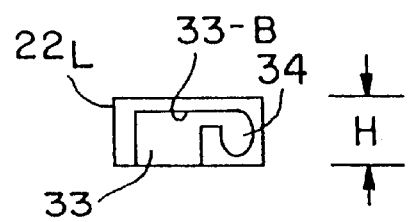

FIG. 32 depicts a further alternative embodiment of the present invention. In particular, FIG. 32 is a sectional view across pod 22L shown in FIG. 22 along line O—O. As seen, in this embodiment, pod 22L features a suction port 33 open along the bottom surface of the suction pod. Suction port 33 further communicates with a suction aperture 31. In this embodiment the total height H of the pod is minimized because the suction aperture is located along side the suction port such that the aperture only exists at a point within the suction port no greater than the height of the suction port opening, that is the bottom of the suction port, depicted here as 33-$b$ is relatively above, in this figure, suction aperture 34. H is between approximately 1 and 4 millimeters, with 2–3 preferred.

Figure 33:
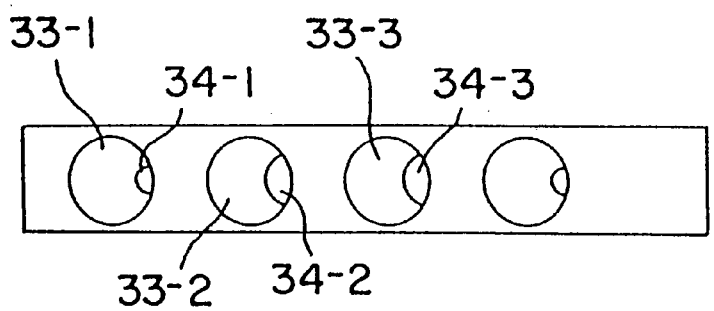

FIGS. 33–37 depict alternative embodiments of the suction pods. These alternative embodiments may be used together or in any combination of any of the above and below shown suction pods. Exact usage of these types of suction pods would be at the preference of the surgeon. In FIG. 33 an embodiment is show in which each of the suction ports 33-1 through 33-5 have the same diameter. In this embodiment, however, the suction apertures 34-1 through 34-4 have different opening sizes into the relative suction ports. In particular, in this embodiment suction aperture 34-2 and 34-3 are relatively much larger than the corresponding suction apertures 34-1 and 34-5. The relatively larger suction apertures are provided in that they provide a more quick capture and fixation of the relevant suction port to the tissue. In contrast, suction ports having relatively smaller suction apertures require more time to effectively capture the tissue. While shown in this FIG. 33 as having relatively larger suction apertures in the two central ports, the opposite may also be provided such that the relatively larger suction apertures are at the end suction ports. The benefit of this configuration is that ports 33-1 and 33-4 are least likely to spontaneously lose capture, while the inner ports 33-2 and 33-3 will quickly achieve capture.

Figure 34:
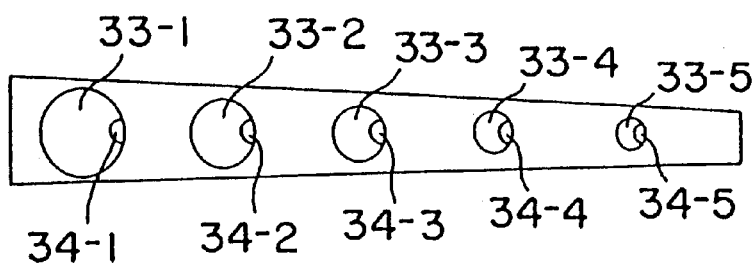

FIG. 34 shows an additional embodiment of the present invention. In this embodiment suction pod is non-rectangular, and in particular, shown as having a relatively, tapered, elongated orientation. Furthermore, such ports are provided which have variable diameters. In particular, in this embodiment, suction port 33-1 has relatively larger diameter, and the diameter of the subsequent suction ports 33-2 at Et seq. become relatively smaller until suction port 33-5 as shown as having the smallest suction port diameter. In this embodiment the corresponding suction apertures 34-1 through 34-5 are provided having a consistent diameter and those surface area opening into the suction ports. Of course, as described above these may be varied in size.

Figure 35:
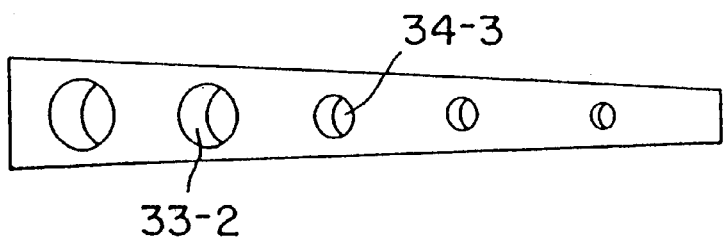

FIG. 35 shows a suction pod having an ever decreasing sized suction ports and furthermore having ever decreasing sized apertures and ports.

Figure 36:
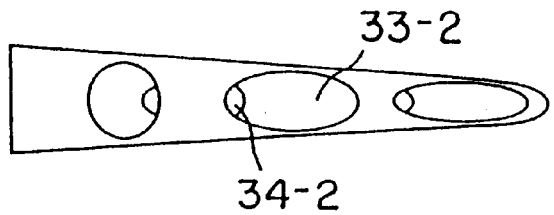

While suction port has been shown above as generally circular it may also be provided in other, non circular forms along the bottom surface of the paddle. In FIG. 36 it is shown that suction port may be provide as elliptical as well as trapezoidal or even square configurations, to name only a few of the many possible alternative embodiments. In each of the embodiments suction port is provided with a single suction aperture. Of course, suction aperture may be provided more than once into the same suction port.

Figure 37:
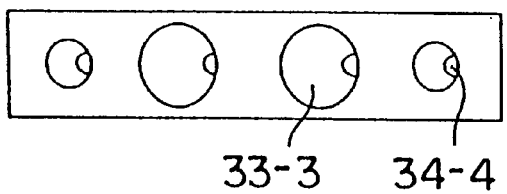

FIG. 37 shows a suction pod having variable diameter suction ports while consistent suction apertures. In this embodiment the central suction port are much larger than the end point suction ports.

Figure 38:
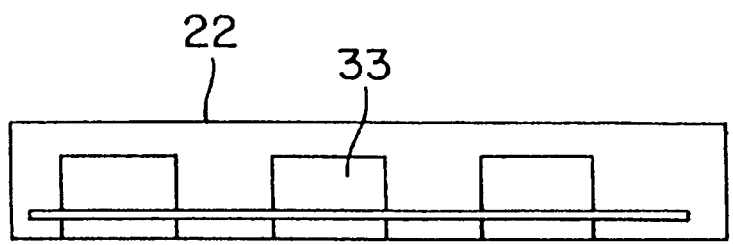
Figure 39:
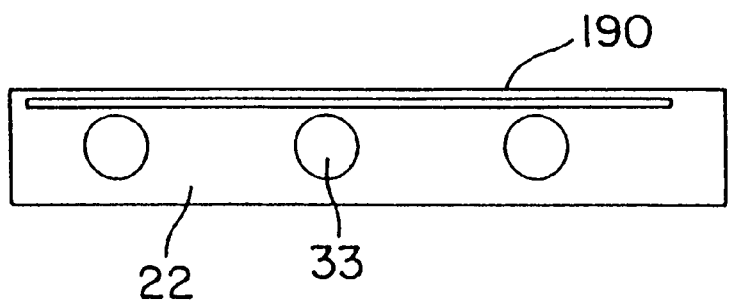
Figure 40:
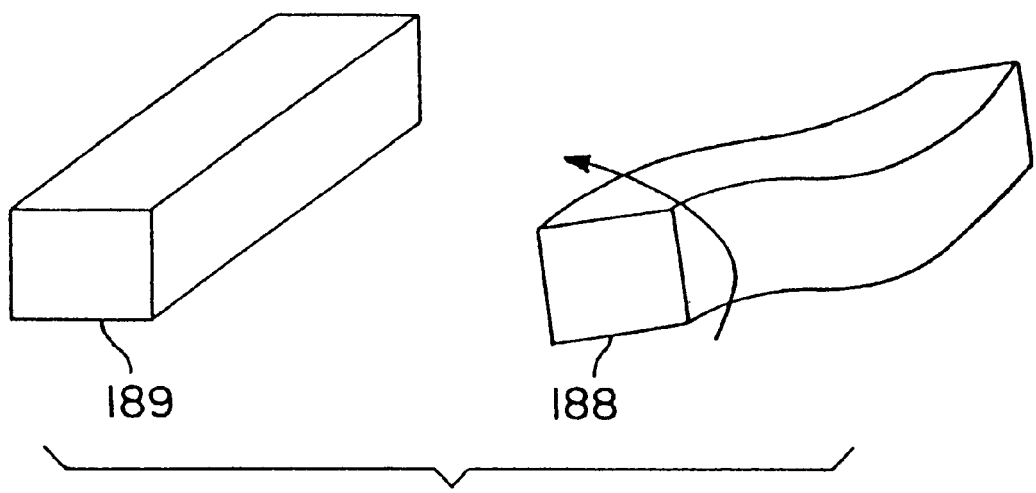

FIGS. 38–40 depict an alternative embodiment of the present invention. As seen, suction pod 22 has a series of suction ports 33 as already described above. In this embodiment suction pod is made, however, from a malleable material such that the pod itself can be shaped by the surgeon prior to disposition of the pod onto the surface of the heart. It is believed that this malleability or conformability provides the surgeon with increased flexibility so as to shape the pod to be conformed into or around the surface of the particular area of the heart upon which he will operate. As seen malleable pod may further include a spring or other form of stiffening element or lockable member 190 which is still malleable to some degree. In the present invention this lockable member 190 would comprise a wound coiled spring, although other materials and devices may be used, including, but not limited to, straps, band, bands, interwoven metallic members, heat set plastics, to name some of other alternative materials and devices which may be used. In a first embodiment the malleable pod is constructed of PVC (poly vinyl chloride) 73 Shore A durometer and the lockable member is constructed from a hypotube made of MP35N metal alloy. In the preferred embodiment the hypotube used to carry suction to the suction ports and thus functions as a suction aperture. Alternately, the malleable pod formation permits the pod itself to be moved from its first orientation, as seen in FIG. 40 at 189 to the deformed position 188 shown at FIG. Alternatively, pod may be manufactured from many other types of materials, including silicone rubber, polyurethane, to name only a few, while lockable member may be constructed form coiled conductors, polymeric strips, or strips or ribbons or springs made from nitinol.

The present invention may be especially suitable for performing a surgical operation on a patient utilizing the simultaneous spreading of the device' paddles and the stiffening of the fixation arm. That is, this embodiment may permit use of the following method of performing a surgical procedure. First, the desired area of tissue is accessed, e.g. the heart and the coronary artery of interest is accessed. Next, a stabilization system is placed upon the surface of the tissue, e.g. a stabilization system as shown in FIGS. 1–3, 6–9 is placed upon the surface of the tissue, and in particular suction pods 22 is placed upon the surface of the tissue. Next, suction is introduced into each pod such that the surface of the tissue is captured by the first pod and the second pod. Next, the first pod and the second pod are caused to be spread relatively apart while the articulating arm 20 is concurrently caused to become stiff. In the illustrated embodiment of FIGS. 1–3 his may be accomplished by turning distal handle 23. As already described above, turning of distal handle causes tension to be applied to cable, causing in turn first paddle and second paddle to thereafter be spread relatively apart or otherwise moved (e.g. moved together, where the exact motion depends on the hinge design and the orientation of the pods or paddles) and also causing each of the links of the arm to be compressed together. The method may also be performed where the step of causing the articulating arm to become stiffer may be performed at either a time prior to or after the step of spreading relatively apart the first pod and the second pod. Thereafter a surgical procedure may be performed. Finally, the process is reversed and the patient is closed, as is well known in the art.

The particular embodiment shown in FIGS. 4 and 5 may be especially suitable for performing a surgical operation on a patient utilizing only the spreading aspect of the device' paddles and not the stabilization through the stiffening of the fixation arm. That is, this embodiment may permit use of the following method of performing a surgical procedure. First, the desired area of tissue is accessed, e.g. the heart and the coronary artery of interest is accessed. Next, a stabilization system is placed upon the surface of the tissue, e.g. a stabilization system as shown in FIGS. 4 and 5 is placed upon the surface of the tissue, and in particular suction pods 22 is placed upon the surface of the tissue. Next, suction is introduced into each pod such that the surface of the tissue is captured by the first pod and the second pod. Next, the first pod and the second pod are caused to be spread relatively apart. In the illustrated embodiment this may be accomplished by turning wheel 5 to cause first paddle and second paddle to thereafter be spread relatively apart. Thereafter a surgical procedure may be performed. Finally, the process is reversed and the patient is closed, as is well known in the art. Thus this method does not require the use of a stiffened arm to provide for the further stabilization. Only the spreading of the paddles is used.

Figure 41:
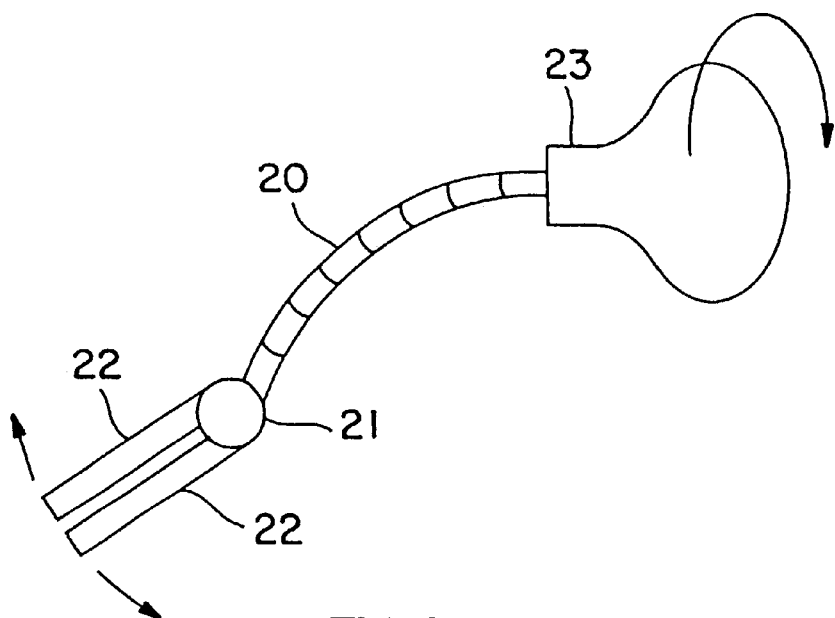

In a further embodiment, the system may be further configured to feature paddles which do not feature suction ports for engaging with and capturing tissue. Rather, in this embodiment, shown in FIG. 41 frictional engagement only by the bottom surface of the paddles is used along with the spreading action to stabilize the tissue. All other aspects of this embodiment may be the same as shown already above. In a further alternative of this design, the tissue-contacting bottom surfaces of the paddles may be treated with materials or textures or both to enhance the friction or gripability between the tissue and the paddle. Such materials or textures may include a series of linear or curvilinear ridges or both, each between 0.5 to 4.0 mm in height, for example. The above dimensions are exemplary and other dimension may also be selected. These embodiments may thus be used to perform a method of performing a surgical procedure upon a patient along the following steps of. First, a desired area of tissue on a patient is accessed. Next, a stabilization system having an articulating arm, the articulating arm having a first pod and a second pod is provided. Preferably one or more of the pods has a bottom surface shaped to conform to the surface of the heart, and further the tissue-contacting bottom surfaces of the paddles are treated with materials or textures or both to enhance the friction. Next the stabilization system is placed upon the surface of the tissue. Next the first pod and the second pod are spread relatively apart. Next the desired surgical procedure is performed. Thereafter the system is removed and the patient is closed.

Figure 42:
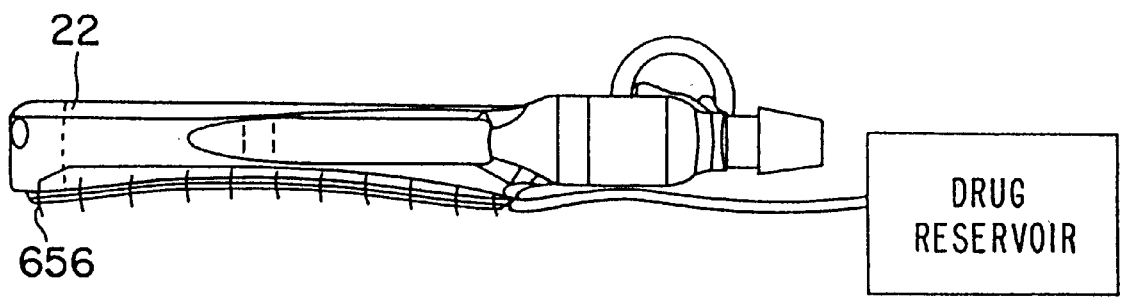

In a still further embodiment, shown here in FIG. 42, the bottom surface may feature a series of burrs or upraised barbs 656. These structures act as cleats which puncture or are introduced a small amount, between 0.25 to 1.5 millimeter beyond the surface of the tissue and into the tissue itself, more or less, and serve to enhance the friction or gripability between the tissue and the paddle. Moreover, still further, these structures may be made hollow and may be coupled to a dispensing reservoir containing drugs, agents or other desired medicinal substance (such as anti-clotting agents, clotting agents, steroids, anti-biotics, growth factors, genetically acting agents or anti arrhythmic agents, to name only a few) so as to also be used to inject directly such substances into the tissue in the vicinity adjacent the surgical procedure, e.g. into the epicardium in the vicinity adjacent the anastomosis. Other than these features, all other aspects of this embodiment may be the same as shown already above.

Figure 43:
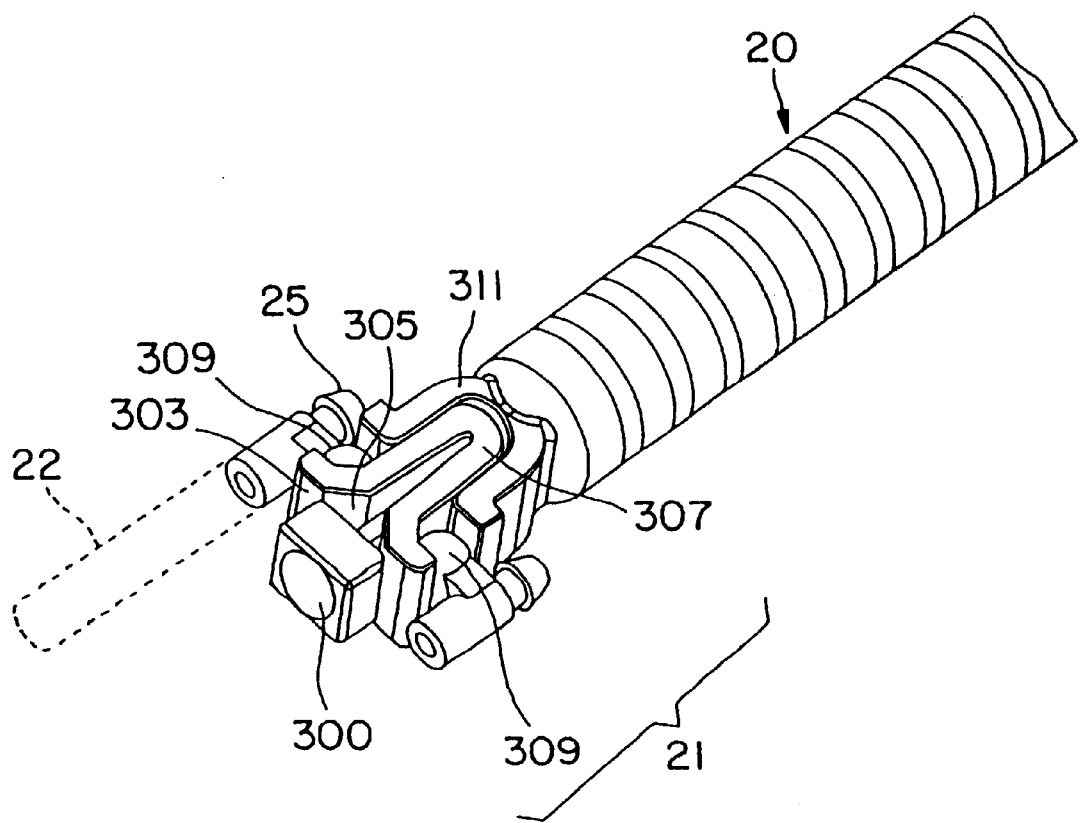

FIG. 43 is a perspective view of an alternative embodiment for tightening/spreading mechanism 21. In this embodiment a series of spreadable wedges having a series of inclines which cooperate with a cable stop to provide a system wherein movement of the pos or paddles may be caused to occur concurrent with or following arm tightening. As seen cable stop 300 is positioned at the distal end of arm. Cable stop hold the distal end of cable, not seen in this FIG. Cable stop is generally a cube like structure, having a relatively sharp corner or edge which is disposed to ride along first inclined surface 303 or second inclined surface 305 of spreadable saddle 307. As seen first inclined surface 303 is disposed at a first angle on spreadable saddle while second inclined surface 305 is disposed at a second angle on spreadable saddle such that the first angle is relatively more flat or oblique in regards to the bottom surface of cable stop 300 when compared to the second angle. Through these inclines and their angular relation to the bottom surface and side edges of cable stop, the co-efficient of friction between the cable stop and the first inclined surface 303 and second inclined surface 305 will be different. In such a manner, a first tension to the cable will generally first cause the arm and its links to be pulled together, thereafter, once tension exceeds the required coefficient of friction and cable stop is moved to engage the second inclined surface will the spreadable saddle be caused to fully begin to spread. As can be seen, a hemispherical mounting 309 is disposed between saddle 307 and U-link 311 such that spreading of saddle pinches mounting and therefore causes movement of the attached pods or paddles (only one of which is depicted here in outline as 22.).

Figure 44:
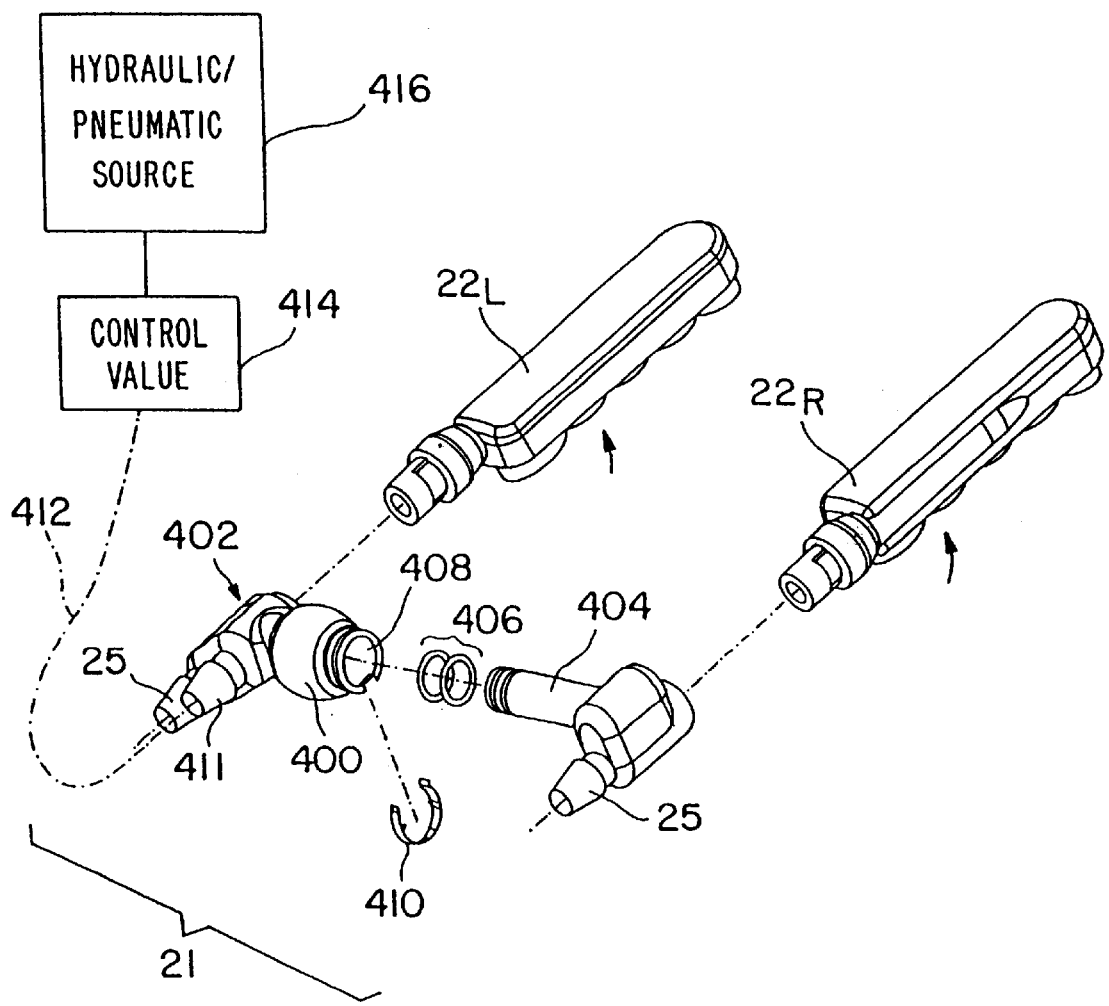

FIG. 44 is a perspective view of an alternative embodiment for tightening/spreading mechanism 21. In this embodiment spread or other movement of the pods or paddles may be accomplished through hydraulic actuation. While shown here as hydraulic actuation, it should also be understood, as used herein, hydraulic also encompasses pneumatic actuation as well. As seen mechanism 21 features a spherical center hinge 400, which is used to couple the shown assembly to an articulated arm, as already described above. That is spherical center hinge 400 may be used in place of split ball. Left pod assembly 402 features a conventional connection 25 to permit suction to attached and communicated to a series of ports, as already described above. This embodiment further features a hydraulic actuator composed of the shaft 404 and seals 406, where the shaft is dimensioned to be slideably moved within runway 408 of left pod assembly. Stop 410 prevents excessive movement of shaft. While shaft itself is depicted as straight, it should be understood it could also be curved so that the right pod or paddle may be made to move in an arc. Runway 408 is coupled by a coupling 411 to hydraulic line 412, which in turn, is coupled to control valve 414 and hydraulic/pneumatic source 416.

Figure 45:
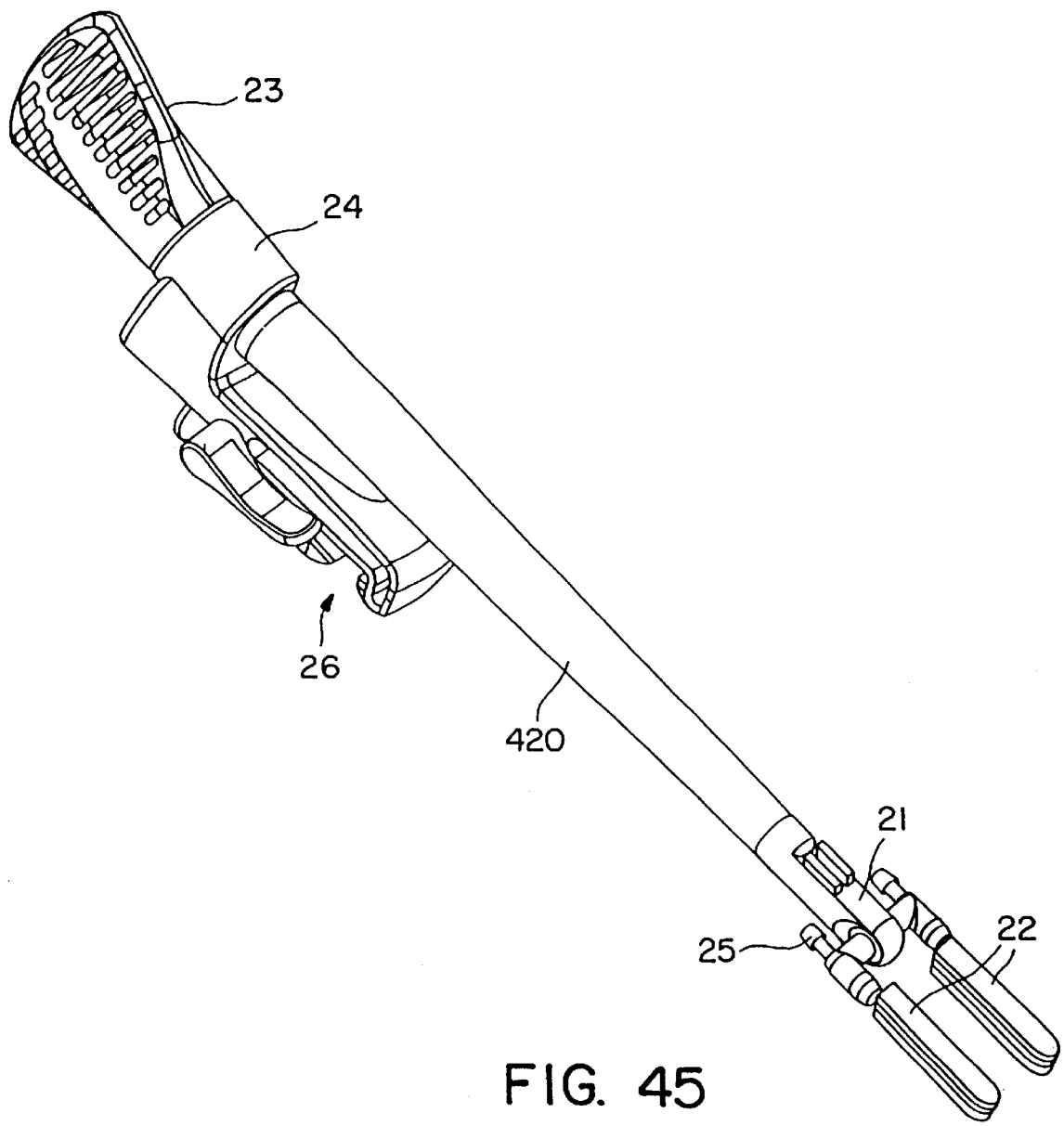

FIG. 45 is a still further embodiment of the present invention. In this embodiment all other features are the same as those described above in regards to FIG. 1 but for that the arm 420 is rigid, as opposed to the flexible arm shown above in FIG. 1. Rigid arm 420 may be used where the are in which the procedure is performed is extremely cramped. Arm 420, because it does not flex may have a much decreased diameter as compared to arm 20 (recall that the FIGS. Are not necessarily to scale.).

The present invention provides the following advantages over conventional suction stabilization systems. First, it reduces the force required to tighten and loosen the articulating arm(s). Second, it improves access to the surgical site in general due to its reduced size, and to the anastomosis site in particular due to the flexibility of the system components and geometry of the system components. Third, it permits relatively delicate manipulations to smoothly spread the suction pods without causing the suction pods to become detached form the arm. Fourth, use of a single arm to support multiple suction pods eliminates interference between opposing arms, such as occurred in the conventional systems when the surgeon tried to position the tissue stabilizers. Fifth, the time to set up the equipment is significantly reduced. Sixth, the design reduces inconsistent performance due to improper maintenance, wear, or unreliable mounting surfaces.

It should be understood, however, that the various features of the invention may be used together, alone or in various combinations. For example, the tissue engagement feature (whether provided through the suction ports, tissue ridges or cleats, for example) may be used alone or in combination with the pod or paddle movement (such as spreading) feature, as well as with the flexible arm feature, or the lockable flexible arm feature. Other features include, but are not limited to, the injection feature, concurrent pod or paddle movement, arm locking or rigidity feature as well as the various features for the paddle or pod movement, any of which may also be provided in combination with any of the other features, where deemed desired. In short, the invention may be used in a myriad of combinations, some of which have been discussed above.

As disclosed, the present invention relates to a method and apparatus for immobilizing tissue. In the preferred embodiment, the invention is used to immobilize heart tissue for a coronary artery bypass graft procedure using either an open or closed chest approach, without the need for a cardiopulmonary bypass. Other surgical techniques, however, which require immobilizing body tissue may also be performed using the present invention, such as surgery on other organs such as the stomach, gall bladder, etc., as well as on other body tissues, such as the eye or the skin, for example. In addition, while the present invention has been described in detail with particular reference to a preferred embodiment and alternative embodiments, it should be understood variations and modifications can be effected within the scope of the following claims. Such modifications may include substituting elements or components which perform substantially the same function in substantially the same way to achieve substantially the same result for those described herein.

What is claimed is:

1. A method for temporarily immobilizing an area of tissue of a beating heart comprising:
providing a paddle assembly having a first paddle and a second paddle, and an arm coupled to the paddle assembly at a distal end thereof;
applying the paddle assembly to the area of tissue to be immobilized; locking the arm in a selected position such that the distal end of the arm is maintained in the selected position; and
spreading the paddles coupled to the arm apart by applying tension to a cable running through the arm.

2. The method according to claim 1 wherein the step of applying the paddle assembly includes applying suction to the beating heart through at least one suction port in each of the paddles.

3. The method according to claim 1 wherein the step of applying the paddle assembly also comprises the step of bending at least one of the paddles to conform to a surface of the heart.

4. The method according to claim 3 wherein the paddle is conformed to the surface of the heart by manually bending a malleable element coupled to the paddle.

5. The method according to claim 1 wherein the step of spreading the paddles apart comprises applying tension to a spreadable saddle.

6. The method according to claim 5 wherein increasing the amount of tension on the spreadable saddle increases the amount of spreading on the paddles.

7. The method according to claim 1 wherein the step of spreading the first paddle and second paddle apart is performed while maintaining the paddles in a generally parallel relation.

8. The method according to claim 1 wherein the arm is at least partially locked before spreading the paddles.

9. A method for temporarily immobilizing an area of tissue of a beating heart comprising:
providing a paddle assembly having a first paddle and a second paddle, and an arm coupled to the paddle assembly at a distal end thereof;
applying the paddle assembly to the area of tissue to be immobilized;
locking the arm in a selected position such that the distal end of the arm is maintained in the selected position; and
spreading the paddles coupled to the arm apart wherein the arm is locked and the paddles are spread by activating a single handle.

10. The method according to claim 9 wherein the handle is activated from a position near a proximal end of the arm.

11. A method for temporarily immobilizing an area of tissue of a beating heart comprising:
providing a paddle assembly having a first paddle and a second paddle, and an arm coupled to the paddle assembly at a distal end thereof;
applying the paddle assembly to the area of tissue to be immobilized;
locking the arm in a selected position such that the distal end of the arm is maintained in the selected position; and
spreading the paddles coupled to the arm apart wherein the arm is locked and the paddles are spread at substantially the same time.

12. A method for temporarily immobilizing an area of tissue of a beating heart comprising:
providing a paddle assembly having a first paddle and a second paddle, and an arm coupled to the paddle assembly at a distal end of the arm
clamping a proximal end of the arm to a surgical retractor;
locking the arm to maintain the position of the paddle assembly on the tissue to be immobilized; and
spreading the paddles coupled to the arm apart by applying tension to a cable running through the arm.

13. The method according to claim 12 wherein the step of applying the paddle assembly includes applying suction to the beating heart through at least one suction port in each of the paddles.

14. The method according to claim 12 wherein the step of applying the paddle assembly also comprises the step of bending at least one of the paddles to conform to a surface of the heart.

15. The method according to claim 14 wherein the paddle is conformed to the surface of the heart by manually bending a malleable element coupled to the paddle.

16. The method according to claim 12 wherein the step of spreading the paddles apart comprises applying tension to a spreadable saddle.

17. The method according to claim 16 wherein increasing the amount of tension on the spreadable saddle increases the amount of spreading on the paddles.

18. The method according to claim 12 wherein the step of spreading the first paddle and second paddle apart is performed while maintaining the paddles in a generally parallel relation.

19. The method according to claim 12 wherein the arm is at least partially locked before spreading the paddles.

20. A method for temporarily immobilizing an area of tissue of a beating heart comprising:
providing a paddle assembly having a first paddle and a second paddle, and an arm coupled to the paddle assembly at a distal end of the arm;
clamping a proximal end of the arm to a surgical retractor;
locking the arm to maintain the position of the paddle assembly on the tissue to be immobilized; and
spreading the paddles coupled to the arm apart wherein the arm is locked and the paddles are spread by activating a single handle.

21. A method for temporarily immobilizing an area of tissue of a beating heart comprising:
providing a paddle assembly having a first paddle and a second paddle, and an arm coupled to the paddle assembly at a distal end of the arm;
clamping a proximal end of the arm to a surgical retractor;
locking the arm to maintain the position of the paddle assembly on the tissue to be immobilized; and
spreading the paddles coupled to the arm apart wherein the arm is locked and the paddles are spread at substantially the same time.

22. The method according to claim 20 wherein the handle is activated from a position near a proximal end of the arm.

* * * * *